(12) United States Patent
Sakakibara et al.

(10) Patent No.: US 7,977,083 B1
(45) Date of Patent: Jul. 12, 2011

(54) METHOD FOR MICROBIAL PRODUCTION OF XYLITOL FROM ARABINOSE

(75) Inventors: Yoshikiyo Sakakibara, Tsukuba (JP); Badal C. Saha, Peoria, IL (US); Paul Taylor, Arlington Heights, IL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 473 days.

(21) Appl. No.: 11/827,506

(22) Filed: Jul. 12, 2007

Related U.S. Application Data

(60) Provisional application No. 60/877,445, filed on Dec. 28, 2006.

(51) Int. Cl.
| | |
|---|---|
| C12N 1/20 | (2006.01) |
| C12N 15/00 | (2006.01) |
| C12N 9/00 | (2006.01) |
| C12N 9/02 | (2006.01) |
| C12N 9/90 | (2006.01) |
| C12N 1/00 | (2006.01) |
| C12N 1/12 | (2006.01) |
| C12N 1/14 | (2006.01) |
| C12P 7/00 | (2006.01) |
| C07H 21/04 | (2006.01) |

(52) U.S. Cl. ............ 435/243; 435/320.1; 435/183; 435/189; 435/233; 435/132; 435/252.1; 435/252.33; 435/254.1; 435/252.3; 536/23.2

(58) Field of Classification Search .......... None
See application file for complete search history.

(56) References Cited

U.S. PATENT DOCUMENTS
| | | | |
|---|---|---|---|
| 5,631,150 | A | 5/1997 | Harkki |
| 6,911,565 | B2 | 6/2005 | Heikkiia et al. |
| 2006/0110809 | A1 | 5/2006 | Taylor |

FOREIGN PATENT DOCUMENTS
| | | |
|---|---|---|
| CN | 1284564 | 2/2001 |

OTHER PUBLICATIONS

Brenda. EC 1.1.1.10, EC 5.3.1.4, and EC 2.7.1.16. obtained from the internet on Dec. 3, 2009.*
Datsenko et al. PNAS. vol. 97, No. 2, pp. 6640-6645, 2000.*
Richard et al. Production of ethanol from L-arabinose by Saccharomyces cerevisiae containing a fungal L-arabinose pathway. FEMS Yeast Res. Apr. 2003;3(2):185-9.*

* cited by examiner

*Primary Examiner* — Yong D Pak
(74) *Attorney, Agent, or Firm* — John Fado; Randall E. Deck; Lesley Shaw

(57) ABSTRACT

Recombinant microorganisms are useful for producing xylitol by fermentation of arabinose. The recombinant microorganisms are produced by transformation of host microorganisms with heterologous polynucleotide sequences coding for each of L-xylulose reductase, D-tagatose 3-epimerase, and L-arabinose isomerase, which transformants express the heterologous polynucleotides at a sufficient functional level to be effective to produce xylitol from arabinose. Production of xylitol is effected by contacting these recombinant microorganisms with a substrate comprising arabinose under conditions effective to produce xylitol from arabinose.

21 Claims, 9 Drawing Sheets ically in many countries. It has the same order of sweetness as sucrose with fewer calories and no unpleasant aftertaste. It is also well-known that xylitol is an anticariogenic sweetener. These properties make xylitol an extremely useful food ingredient.

SEQUENCE LISTING

<160> NUMBER OF SEQ ID NOS: 18

<210> SEQ ID NO 1
<211> LENGTH: 42
<212> TYPE: DNA
<213> ORGANISM: A. monospora

<400> SEQUENCE: 1
gcggatccat aaaggaggat atataatgac tgactacatt cc     42

<210> SEQ ID NO 2
<211> LENGTH: 35
<212> TYPE: DNA
<213> ORGANISM: A. monospora

<400> SEQUENCE: 2
gctctagact accaagaagt gaaaccacca tcaac     35

<210> SEQ ID NO 3
<211> LENGTH: 39
<212> TYPE: DNA
<213> ORGANISM: R. radiobacter

<400> SEQUENCE: 3
gcgaattcta aggaggatat attatgaaac acggcatct     39

<210> SEQ ID NO 4
<211> LENGTH: 23
<212> TYPE: DNA
<213> ORGANISM: R. radiobacter

<400> SEQUENCE: 4
gcggatcctc agccaccaag aac     23

<210> SEQ ID NO 5
<211> LENGTH: 41
<212> TYPE: DNA
<213> ORGANISM: E. coli

<400> SEQUENCE: 5
gcgtctagat aaggaggatc atctatgacg atttttgata a     41

<210> SEQ ID NO 6
<211> LENGTH: 28
<212> TYPE: DNA
<213> ORGANISM: E. coli

<400> SEQUENCE: 6
ggcatgctta gcgacgaaac ccgtaata     28

<210> SEQ ID NO 7
<211> LENGTH: 37
<212> TYPE: DNA
<213> ORGANISM: P. ananatis

<400> SEQUENCE: 7
cggatcctta ggaggatata ttatgagcgg tgaatat                          37

<210> SEQ ID NO 8
<211> LENGTH: 29
<212> TYPE: DNA
<213> ORGANISM: P. ananatis

<400> SEQUENCE: 8
gctctagatt accagatggt aaagccacc                                   29

<210> SEQ ID NO 9
<211> LENGTH: 60
<212> TYPE: DNA
<213> ORGANISM: E. coli

<400> SEQUENCE: 9
gatgtgccgc agggagctga tctgctgaaa gccgtggatg gtgtaggctg gagctgcttc   60

<210> SEQ ID NO 10
<211> LENGTH: 60
<212> TYPE: DNA
<213> ORGANISM: E. Coli

<400> SEQUENCE: 10
gatgagtggt cgagggccag ttgcagaagt ggtcggctca attccgggga tccgtcgacc   60

<210> SEQ ID NO 11
<211> LENGTH: 60
<212> TYPE: DNA
<213> ORGANISM: E. Coli

<400> SEQUENCE: 11
actgtttctc catacccgtt tttttggatg gagtgaaacg gtgtaggctg gagctgcttc   60

<210> SEQ ID NO 12
<211> LENGTH: 60
<212> TYPE: DNA
<213> ORGANISM: E. coli

<400> SEQUENCE: 12
ctggtttcgt ttgattggct gtggttttat acagtcatta catatgaata tcctccttag   60

<210> SEQ ID NO 13
<211> LENGTH: 1503
<212> TYPE: DNA
<213> ORGANISM: E. coli

<400> SEQUENCE: 13
atgacgattt ttgataatta tgaagtgtgg tttgtcattg gcagccagca tctgtatggc   60
ccggaaaccc tgcgtcaggt cacccaacat gccgagcacg ttgttaatgc gctgaatacg  120
gaagcgaaac tgccctgcaa actggtgttg aaaccgctgg caccacgcc ggatgaaatc  180 accgctattt gccgcgacgc gaattacgac gatccgtgcg ctggtctggt ggtgtggctg  240
cacaccttct ccccggccaa aatgtggatc aacggcctga ccatgctcaa caaaccgttg  300
ctgcaattcc acacccagtt caacgcggcg ctgccgtggg acagtatcga tatggacttt  360

```
atgaacctga accagactgc acatggcggt cgcgagttcg gcttcattgg cgcgcgtatg    420
cgtcagcaac atgccgtcgt taccggtcac tggcaggata acaagccca tgagcgtatc    480 ggctcctgga tgcgtcaggc ggtttctaaa caggatcccc gtcatctgaa agtctgccgt    540
tttggcgata acatgcgtga agtggcggtc accgatggtg ataaagttgc cgcacagatc    600
aagttcggtt tctccgtcaa tacctgggcg gttggcgatc tggtgcaggt ggtgaactcc    660
atcagcgacg gcgatgttaa cgcgctggtc gatgagtacg aaagctgcta caccatgacg    720
cctgcaacac aaatccacgg cgaaaaacga cagaacgtgc tggaagcggc gcgtattgag    780
ctggggatga agcgtttcct ggaacaaggt ggcttccacg cgttcaccac cacctttgaa    840
gatttgcacg tctgaaaaca gcttccaggt ctggccgtac agcgtctgat gcagcagggt    900
tacggctttg cgggcgaagg cgactggaaa accgccgccc tgcttcgcat catgaaggtg    960
atgtcaaccg tctgcaggg cggcaccctcc tttatggagg actacaccta tcacttcgag   1020
aaaggtaatg acttggtgct cggctcccat atgctgaaag tctgcccgtc gattgccgta   1080
gaagagaaac cgatcctcga cgttcagcat ctcggtattg gtggtaagga cgatcctgcc   1140
cgactgatct tcaataccca aaccggtcca gcgattgtcg ccagcctgat tgatctcggc   1200
gatcgttacc gtctgctggt taactgtatc gacacggtga aaacaccgca ctccctgccg   1260
aaactgccgg tggcgaatgc gctgtggaaa gcgcaaccgg atctgccaac tgcttccgaa   1320
gcgtggatcc tcgctggtgg cgcgcaccat accgtcttca gccatgcgct gaacctcaac   1380
gatatgcgcc agttcgccga gatgcacgac attgaaatca cggtgattga taacgatacc   1440
cgcctgccag cgtttaaaga cgcgctgcgc tggaacgaag tgtattacgg atttcgtcgc   1500
taa                                                                  1503
```

<210> SEQ ID NO 14
<211> LENGTH: 500
<212> TYPE: PRT
<213> ORGANISM: E. coli

<400> SEQUENCE: 14

```
Met Thr Ile Phe Asp Asn Tyr Glu Val Trp Phe Val Ile Gly Ser Gln
1               5                   10                  15

His Leu Tyr Gly Pro Glu Thr Leu Arg Gln Val Thr Gln His Ala Glu
            20                  25                  30

His Val Val Asn Ala Leu Asn Thr Glu Ala Lys Leu Pro Cys Lys Leu
        35                  40                  45

Val Leu Lys Pro Leu Gly Thr Thr Pro Asp Glu Ile Thr Ala Ile Cys
    50                  55                  60

Arg Asp Ala Asn Tyr Asp Asp Pro Cys Ala Gly Leu Val Val Trp Leu
65                  70                  75                  80

His Thr Phe Ser Pro Ala Lys Met Trp Ile Asn Gly Leu Thr Met Leu
                85                  90                  95

Asn Lys Pro Leu Leu Gln Phe His Thr Gln Phe Asn Ala Ala Leu Pro
            100                 105                 110

Trp Asp Ser Ile Asp Met Asp Phe Met Asn Leu Asn Gln Thr Ala His
        115                 120                 125

Gly Gly Arg Glu Phe Gly Phe Ile Gly Ala Arg Met Arg Gln Gln His
    130                 135                 140

Ala Val Val Thr Gly His Trp Gln Asp Lys Gln Ala His Glu Arg Ile
145                 150                 155                 160

Gly Ser Trp Met Arg Gln Ala Val Ser Lys Gln Asp Thr Arg His Leu
```

```
                          165                 170                 175
Lys Val Cys Arg Phe Gly Asp Asn Met Arg Glu Val Ala Val Thr Asp
            180                 185                 190
Gly Asp Lys Val Ala Ala Gln Ile Lys Phe Gly Phe Ser Val Asn Thr
                195                 200                 205
Trp Ala Val Gly Asp Leu Val Gln Val Val Asn Ser Ile Ser Asp Gly
    210                 215                 220
Asp Val Asn Ala Leu Val Asp Glu Tyr Glu Ser Cys Tyr Thr Met Thr
225                 230                 235                 240
Pro Ala Thr Gln Ile His Gly Glu Lys Arg Gln Asn Val Leu Glu Ala
                245                 250                 255
Ala Arg Ile Glu Leu Gly Met Lys Arg Phe Leu Glu Gln Gly Gly Phe
            260                 265                 270
His Ala Phe Thr Thr Thr Phe Glu Asp Leu His Gly Leu Lys Gln Leu
        275                 280                 285
Pro Gly Leu Ala Val Gln Arg Leu Met Gln Gly Tyr Gly Phe Ala
    290                 295                 300
Gly Glu Gly Asp Trp Lys Thr Ala Ala Leu Leu Arg Ile Met Lys Val
305                 310                 315                 320
Met Ser Thr Gly Leu Gln Gly Gly Thr Ser Phe Met Glu Asp Tyr Thr
                325                 330                 335
Tyr His Phe Glu Lys Gly Asn Asp Leu Val Leu Gly Ser His Met Leu
            340                 345                 350
Glu Val Cys Pro Ser Ile Ala Val Glu Glu Lys Pro Ile Leu Asp Val
        355                 360                 365
Gln His Leu Gly Ile Gly Gly Lys Asp Asp Pro Ala Arg Leu Ile Phe
    370                 375                 380
Asn Thr Gln Thr Gly Pro Ala Ile Val Ala Ser Leu Ile Asp Leu Gly
385                 390                 395                 400
Asp Arg Tyr Arg Leu Leu Val Asn Cys Ile Asp Thr Val Lys Thr Pro
                405                 410                 415
His Ser Leu Pro Lys Leu Pro Val Ala Asn Ala Leu Trp Lys Ala Gln
            420                 425                 430
Pro Asp Leu Pro Thr Ala Ser Glu Ala Trp Ile Leu Ala Gly Gly Ala
        435                 440                 445
His His Thr Val Phe Ser His Ala Leu Asn Leu Asn Asp Met Arg Gln
    450                 455                 460
Phe Ala Glu Met His Asp Ile Glu Ile Thr Val Ile Asp Asn Asp Thr
465                 470                 475                 480
Arg Leu Pro Ala Phe Lys Asp Ala Leu Arg Trp Asn Glu Val Tyr Tyr
                485                 490                 495
Gly Phe Arg Arg
        500

<210> SEQ ID NO 15
<211> LENGTH: 870
<212> TYPE: DNA
<213> ORGANISM: Agrobacterium tumefaciens str. C58

<400> SEQUENCE: 15
atgaaacacg gcatctatta ttcttactgg gaacatgagt ggagcgccaa gttcggtccc      60
tatatcgaga aggtcgccaa gctcggtttc gacatcatcg aagtcgccgc ccaccatatc     120
aacgaataca gcgacgccga actcgcgacc atcaggaaga gcgcgaagga taacggcatc     180
atcctcaccg ccggcatcgg tccgtcgaaa accaagaacc tgtcgtcgga agatgctgcg     240
```

```
gtgcgtgcgg ccggcaaggc gttctttgaa agaacccttt cgaacgtcgc caagctcgat    300
atccacacca tcgcggcgc attgcattcc tattggccaa tcgattattc gcagcccgtc    360
gacaaggcag cgattatgc gcgcggcgtc gagggtatca acggcattgc cgatttcgcc    420
aatgatctcg gcatcaacct gtgcatcgaa gtcctcaacc gctttgaaaa ccacgtcctc    480
aacacggcgg cggaaggcgt cgcttttgtg aaggatgtcg gcaagaacaa tgtgaaagtc    540
atgctggata ccttccacat gaacatcgag gaagacagtt tcggtgacgc catccgcacg    600
gccggcccgc ttctggggca cttccatacc ggtgaaagca atcgccgcgt accgggcaag    660
ggcagaatgc cgtggcacga atcggccttg cgctgcgtg atatcaacta caccggcgcg    720
gtaatcatgg agccttcgt caagacaggc ggcaccatcg gctcggatat caaggtgtgg    780
cgcgacctga gcgtggcgc cgacatcgcg aaaatggatg aagatgcccg caatgcgctg    840
gcattctccc gcttcgttct tggtggctga                                    870
```

<210> SEQ ID NO 16
<211> LENGTH: 289
<212> TYPE: PRT
<213> ORGANISM: Agrobacterium tumefaciens str. C58

<400> SEQUENCE: 16

```
Met Lys His Gly Ile Tyr Tyr Ser Tyr Trp Glu His Glu Trp Ser Ala
  1               5                  10                  15

Lys Phe Gly Pro Tyr Ile Glu Lys Val Ala Lys Leu Gly Phe Asp Ile
                 20                  25                  30

Ile Glu Val Ala Ala His His Ile Asn Glu Tyr Ser Asp Ala Glu Leu
             35                  40                  45

Ala Thr Ile Arg Lys Ser Ala Lys Asp Asn Gly Ile Ile Leu Thr Ala
         50                  55                  60

Gly Ile Gly Pro Ser Lys Thr Lys Asn Leu Ser Ser Glu Asp Ala Ala
 65                  70                  75                  80

Val Arg Ala Ala Gly Lys Ala Phe Phe Glu Arg Thr Leu Ser Asn Val
                 85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
        130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Ser Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
```

```
                    260              265              270
Asp Glu Asp Ala Arg Asn Ala Leu Ala Phe Ser Arg Phe Val Leu Gly
        275              280              285

Gly

<210> SEQ ID NO 17
<211> LENGTH: 816
<212> TYPE: DNA
<213> ORGANISM: Ambrosiozyma monospora

<400> SEQUENCE: 17
atgactgact acattccaac ttttagattc gatggccact taaccattgt cacaggtgcc      60
tgtggtggtt tagctgaagc tttaatcaag ggtttgttgg cctacggttc tgacattgct     120
ttgcttgata tcgaccaaga aaagactgct gccaaacaag ccgaatacca caaatacgct     180
actgaagaat tgaagttgaa agaagttcca aagatgggtt catatgcctg tgatatttct     240
gattctgata ccgttcacaa ggtgtttgct caagttgcta aggattttgg taagttgcca     300
ttgcacttgg ttaacacagc tggttactgt gaaaacttcc catgtgaaga ttacccagcc     360
aagaacgctg agaagatggt gaaggttaac ttgttgggtt cttttgtatgt ttctcaagcc     420 tttgctaagc cattgatcaa agaaggtatc aagggtgctt ctgttgtttt gattggttct     480
atgtctggtg ccattgtcaa cgatcctcaa aaccaagttg tctacaacat gtccaaggct     540
ggtgttatcc atttggctaa gactttggct tgtgaatggg ctaagtacaa catcagagtt     600
aattctttaa acccaggtta catctacggt cctttgacca agaatgttat caatggtaac     660
gaagaattgt acaacagatg gatctctggt atcccacaac aaagaatgtc cgaaccaaag     720
gaatacattg gtgctgtttt gtacttgctt tctgaatctg ctgcttcata cactactggt     780
gccagcttac tggttgatgg tggtttcact tcttgg                                816

<210> SEQ ID NO 18
<211> LENGTH: 272
<212> TYPE: PRT
<213> ORGANISM: Ambrosiozyma monospora

<400> SEQUENCE: 18

Met Thr Asp Tyr Ile Pro Thr Phe Arg Phe Asp Gly His Leu Thr Ile
1               5                   10                  15

Val Thr Gly Ala Cys Gly Gly Leu Ala Glu Ala Leu Ile Lys Gly Leu
            20                  25                  30

Leu Ala Tyr Gly Ser Asp Ile Ala Leu Leu Asp Ile Asp Gln Glu Lys
        35                  40                  45

Thr Ala Ala Lys Gln Ala Glu Tyr His Lys Tyr Ala Thr Glu Glu Leu
    50                  55                  60

Lys Leu Lys Glu Val Pro Lys Met Gly Ser Tyr Ala Cys Asp Ile Ser
65                  70                  75                  80

Asp Ser Asp Thr Val His Lys Val Phe Ala Gln Val Ala Lys Asp Phe
                85                  90                  95

Gly Lys Leu Pro Leu His Leu Val Asn Thr Ala Gly Tyr Cys Glu Asn
            100                 105                 110

Phe Pro Cys Glu Asp Tyr Pro Ala Lys Asn Ala Glu Lys Met Val Lys
        115                 120                 125

Val Asn Leu Leu Gly Ser Leu Tyr Val Ser Gln Ala Phe Ala Lys Pro
    130                 135                 140

Leu Ile Lys Glu Gly Ile Lys Gly Ala Ser Val Val Leu Ile Gly Ser
145                 150                 155                 160
```

```
Met Ser Gly Ala Ile Val Asn Asp Pro Gln Asn Gln Val Val Tyr Asn
            165                 170                 175

Met Ser Lys Ala Gly Val Ile His Leu Ala Lys Thr Leu Ala Cys Glu
            180                 185                 190

Trp Ala Lys Tyr Asn Ile Arg Val Asn Ser Leu Asn Pro Gly Tyr Ile
            195                 200                 205

Tyr Gly Pro Leu Thr Lys Asn Val Ile Asn Gly Asn Glu Glu Leu Tyr
        210                 215                 220

Asn Arg Trp Ile Ser Gly Ile Pro Gln Gln Arg Met Ser Glu Pro Lys
225                 230                 235                 240

Glu Tyr Ile Gly Ala Val Leu Tyr Leu Leu Ser Glu Ser Ala Ala Ser
                245                 250                 255

Tyr Thr Thr Gly Ala Ser Leu Leu Val Asp Gly Gly Phe Thr Ser Trp
            260                 265                 270
```

METHOD FOR MICROBIAL PRODUCTION OF XYLITOL FROM ARABINOSE

CROSS-REFERENCE TO RELATED APPLICATION

This application claims the benefit under 35 U.S.C. 1.19(e) of U.S. provisional No. 60/877,445, filed Dec. 28, 2006, the contents of which are incorporated by reference herein.

BACKGROUND OF THE INVENTION

1. Field of the Invention

The invention is drawn to recombinant microorganisms effective for producing xylitol from arabinose.

2. Description of the Prior Art

Xylitol is a non-sugar sweetener approved for use in foods and other items in many countries. It has the same order of sweetness as sucrose with fewer calories and no unpleasant aftertaste. It is also well-known that xylitol is an anticariogenic sweetener. These properties make xylitol an extremely useful food ingredient.

Microbial production of xylitol, using hemicellulosic biomass such as agricultural residues, is attractive for reducing its manufacturing cost. The hemicellulose hydrolyzates are generally rich in D-xylose and L-arabinose (Saha, 2003, J. Ind. Microbiol. Biotechnol. 30:279-291). D-xylose can be metabolized in xylose-fermenting yeasts such as *Candida*, *Debaromyces*, and *Pichia* species. These yeasts have xylose reductase, which reduces D-xylose to xylitol. Xylitol production from D-xylose has been well studied using the xylose-fermenting yeasts and their reductases [Saha & Bothast, Microbial production of xylitol. In: Saha, B. C. and Woodward, J. (eds.) Fuels and Chemicals, ACS Symposium Series 666, American Chemical Society, pp. 307-319, 1997]. However, in these systems, the arabinose is a particular problem to xylitol production because it can be easily converted to arabitol, which is very difficult to separate from the xylitol in a cost efficient manner.

In contrast to xylose, no xylitol production process from L-arabinose has been developed, despite its high abundance in the hemicellulosic hydrolyzates. Certain species of fungi have been reported to possess an L-arabinose catabolic pathway that synthesizes xylitol as an intermediate (Chang & Knight, 1960, Biochem. Biophys. Res. Commun. 3:554-559). However, no bacteria have been reported for producing xylitol from arabinose. Thus, the need remains for an improved fermentative process for producing xylitol from arabinose.

SUMMARY OF THE INVENTION

We have discovered recombinant microorganisms which are useful for producing xylitol by fermentation of arabinose. The recombinant microorganisms are produced by transformation of host microorganisms with heterologous polynucleotide sequences coding for each of L-xylulose reductase, D-tagatose 3-epimerase, and L-arabinose isomerase, which transformants express the heterologous polynucleotides at a sufficient functional level to be effective to produce xylitol from arabinose. Production of xylitol is effected by contacting these recombinant microorganisms with a substrate comprising arabinose under conditions effective to produce xylitol from arabinose.

We have also produced nucleic acid constructs or expression cassettes which comprise the polynucleotide sequences coding for each of L-xylulose reductase, D-tagatose 3-epimerase, and L-arabinose isomerase, operably linked to one or more expression control sequences. These polynucleotide sequences direct the expression of polypeptides having L-xylulose reductase, D-tagatose 3-epimerase, and L-arabinose isomerase activity in an expression host and such that the transformed host is capable of converting L-arabinose to xylitol.

In accordance with this discovery, it is an object of this invention to provide improved recombinant microorganisms that are effective for the production of xylitol from arabinose.

Another object of this invention to provide improved expression cassettes effective for transforming microorganisms and producing recombinant microorganisms that are effective for the production of xylitol from arabinose.

Still another object of this invention to provide improved recombinant microorganisms that are effective for the production of xylitol from hemicellulosic hydrolyzates containing arabinose.

Yet another object of this invention to provide improved recombinant microorganisms that are effective for the production of xylitol from arabinose which microorganisms lack one or more enzymes in the pathway for converting L-ribulose or L-xylulose or both to D-xylulose 5-phosphate.

Other objects and advantages of this invention will become readily apparent from the ensuing description.

DEFINITIONS

Figure 1:
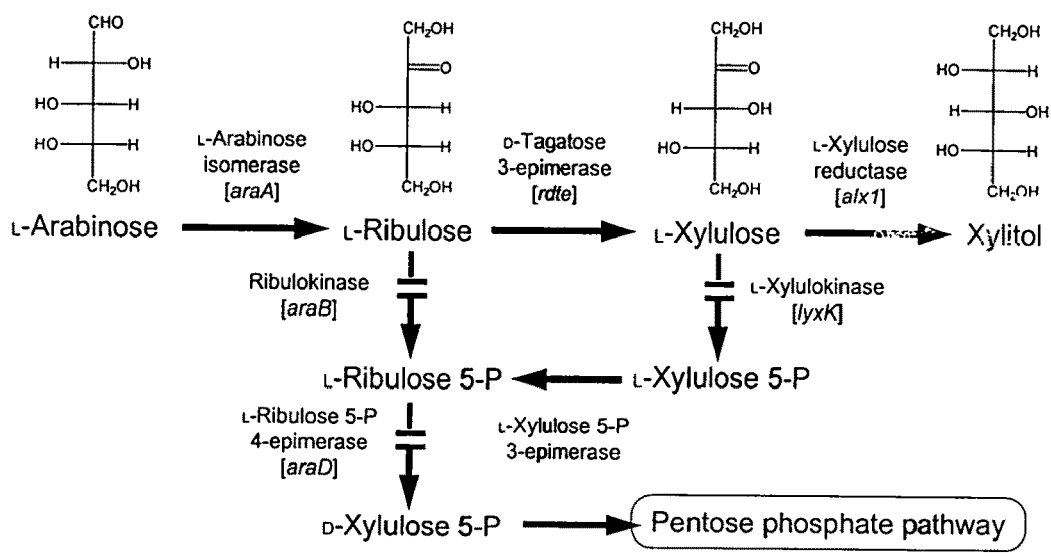
FIG. 1 shows the novel biosynthetic pathway of xylitol from L-arabinose. L-Arabinose isomerase from *Escherichia coli* (araA), D-tagatose 3-epimerase from *Rhizobium radiobacter* (rdte) and L-xylulose reductase from *Ambrosiozyma monospora* (alx1) genes were cloned into the pBAD-Kan plasmid and transformed into *E. coli* ZUC99. The endogenous arabinose catabolic operon (araBAD) and L-xyluloki-nase gene (lyxK) in *E. coli* strain ZUC99 were disrupted in order to prevent degradation of the intermediates of the xylitol synthetic pathway.

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., uracil utilization, tetracycline resistance, ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

Complement or Complementary Sequence. The product of complementary base pairing in which purines bond with pyrimidines, as occurs in the two polynucleotide chains of DNA (adenine with thymine, guanine with cytosine) and between DNA and messenger RNA nucleotides during transcription.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences and cDNA from eucaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses.

Expression. The process undergone by a structural gene to produce a polypeptide. Expression requires both transcription of DNA and translation of RNA.

Expression Vector. A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Phage or Bacteriophage. Bacterial virus many of which include DNA sequences encapsidated in a protein envelope or coat ("capsid"). In a unicellular organism, a phage may be introduced by a process called transfection.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant".

Polypeptide. A linear series of amino acids connected one to the other by peptide bends between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Start Codon. Also called the initiation codon, is the first mRNA triplet to be translated during protein or peptide synthesis and immediately precedes the structural gene being translated. The start codon is usually AUG, but may sometimes also be GUG.

Structural Gene. A DNA sequence which encodes through its template or messenger RNA (mRNA) a sequence of amino acids characteristic of a specific polypeptide.

Substantially Pure. The condition of a compound, such as a protein or a nucleotide, being cell free or being separated from other components that would interfere with or have a substantial qualitative effect on the activity of the compound or on a substrate on which the compound acts.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In procaryotes and some fungi, for example, the exogenous DNA may be maintained on an episomal element such as a plasmid. With respect to most eucaryotic cells, a stably transformed cell is one in which the exogenous DNA has been integrated into a chromosome so that it is inherited by daughter cells through chromosome replication. This stability is demonstrated by the ability of the eucaryotic cell to establish cell lines or clones comprised of a population of daughter cells containing the exogenous DNA.

Transcription. The process of producing mRNA from a structural gene.

Translation. The process of producing a polypeptide from mRNA.

DETAILED DESCRIPTION OF THE INVENTION

To confer the ability to produce xylitol from arabinose in accordance with this invention, microorganisms are transformed with heterologous polynucleotide sequences coding for three enzymes: L-xylulose reductase, D-tagatose 3-epimerase, and L-arabinose isomerase. As shown in FIG. 1, L-arabinose isomerase catalyzes the conversion of L-arabinose to L-ribulose, which is in turn converted to L-xylulose by D-tagatose 3-epimerase, and the L-xylulose is subsequently converted to xylitol by L-xylulose reductase.

L-xylulose reductases, D-tagatose 3-epimerases, and L-arabinose isomerases and their corresponding genes which are suitable for use herein have been described previously and may be derived from a variety of sources. In general, any L-arabinose isomerase effective for catalyzing the conversion of L-arabinose to L-ribulose, any D-tagatose 3-epimerase effective for converting L-ribulose to L-xylulose, and any L-xylulose reductase effective for catalyzing the conversion of L-xylulose to xylitol, in the selected host microorganism are suitable for use herein.

The preferred L-arabinose isomerase (AraA) for use in the invention was originally isolated from *E. coli*, and the gene sequence and predicted amino acid sequence of the enzyme was described by Lee et al. (1986, Gene 47:231-244), and deposited in GenBank under accession number M15263, the contents of each of which are incorporated by reference herein (which gene and predicted amino acid sequences are included herein as SEQ ID Nos. 13 and 14, respectively). The preferred D-tagatose 3-epimerase (Rdte) for use in the invention has been isolated from *Rhizobium radiobacter* (previously known as *Agrobacterium tumefaciens*) as described in Example 1. The gene sequence and predicted amino acid sequence of the enzyme was deposited in GenBank under accession number AE008210, the contents of which are incorporated by reference herein (which gene and predicted amino acid sequences are included herein as SEQ ID Nos. 15 and 16, respectively). The gene coding for a homologous D-tagatose 3-epimerase from *Pseudomonas cichorii* has also been described and sequenced by Ishida et al. (1997, J. Ferment. Bioeng. 83:529-534, the contents of which are incorporated by reference herein), and is also suitable for use herein. The preferred L-xylulose reductase (Alx1) for use in the invention was originally isolated from *Ambrosiozyma monospora* and described by Verho et al. (2004, J. Biol. Chem. 279:14746-14751), and the gene sequence and predicted amino acid sequence of the enzyme was deposited in GenBank under accession number AJ583159, the contents of each of which are incorporated by reference herein (which gene and predicted amino acid sequences are included herein as SEQ ID Nos. 17 and 18, respectively). The gene coding for L-xylulose reductase (Plxr) from *Pantoea ananatis*, described in Example 4, is also suitable for use herein. Alternatively, the process may utilize enzymes having at least 90%, preferably at least 95%, identity with the amino acid sequence deposited in GenBank under accession nos. M15263, AE008210, and AJ583159, and which L-arabinose isomerase is still effective for catalyzing the conversion of L-arabinose to L-ribulose, or D-tagatose 3-epimerase is still effective for converting L-ribulose to L-xylulose, or L-xylulose reductase is still effective for catalyzing the conversion of L-xylulose to xylitol.

Two polypeptides are said to be "identical" if the sequence of amino acid residues, respectively, in the two sequences is the same when aligned for maximum correspondence as described below. Sequence comparisons between two (or more) polypeptides are typically performed by comparing sequences of the two sequences over a segment or "comparison window" to identify and compare local regions of sequence similarity. Optimal alignment of sequences for comparison may be conducted by the local homology algorithm of Smith and Waterman (1981, Adv. Appl. Math., 2:482), by the homology alignment algorithm of Needleman and Wunsch (1970, J. Mol. Biol., 48:443), by the search for similarity method of Pearson and Lipman [1988, Proc. Natl. Acad. Sci. (U.S.A.) 85:2444], by computerized implementations of these algorithms [(GAP, BESTFIT, FASTA, and TFASTA in the Wisconsin Genetics Software Package, Genetics Computer Group (GCG), 575 Science Dr., Madison, Wis.], or by inspection. "Percentage of sequence identity" is determined by comparing two optimally aligned sequences over a comparison window, wherein the portion of the polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

The term "substantial identity" of amino acid sequences for these purposes normally means sequence identity of at least 90%, and most preferably at least 95% compared to a reference sequence. The reference sequence herein is the predicted amino acid sequence of the L-xylulose reductase, D-tagatose 3-epimerase, and L-arabinose isomerase deposited in GenBank under accession nos. AJ583159, AE008210, and M15263, respectively. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The DNA sequences of the L-xylulose reductase, D-tagatose 3-epimerase, and L-arabinose isomerase genes can be used to prepare recombinant DNA molecules by cloning into any suitable vector. A variety of vector-host cell expression systems may be employed in practicing the present invention. Strains of bacteria, including *Escherichia coli* such as described in the Examples hereinbelow are particularly useful in producing xylitol. However, the novel invention described here can be applied with numerous hosts that would be desirable. Host strains may be of bacterial, fungal, or yeast origin. Factors that can be considered in choosing host strains include substrate range, hardiness, sugar tolerance, salt tolerance, temperature tolerance, pH tolerance, and lactate tolerance. Ascertaining the most appropriate host-vector system is within the skill of the person in the art.

In one preferred embodiment, host microorganisms are selected which lack one or more enzymes of the L-arabinose catabolic pathway for converting L-ribulose and/or L-xylulose intermediates to D-xylulose 5-phosphate. An example of one such microorganism is described in Example 7. In this embodiment the most preferred host microorganisms would substantially lack both ribulokinase (AraB) activity for the phosphorylation of L-ribulose to L-ribulose-5-phosphate, and L-xylulokinase (LyxK) activity for the phosphorylation of L-xylulose to L-xylulose-5-phosphate. In an alternative preferred embodiment such as described in Example 2, for host microorganisms which typically possess the L-arabinose catabolic pathway for converting L-ribulose and/or L-ribulose-5-phosphate intermediates to D-xylulose-5-phosphate, the ribulokinase and/or L-ribulose-5-phosphate 4-epimerase genes may be disrupted to prevent conversion of intermediates to D-xylulose 5-phosphate as shown in FIG. 1. Lacking substantial ribulokinase and/or L-ribulose-5-phosphate 4-epimerase activity, the resultant mutant may then be used as the host microorganism for transformation with the nucleotide sequences coding for L-xylulose reductases, D-tagatose 3-epimerases, and L-arabinose isomerases as described hereinbelow.

In another embodiment of the invention the microorganism comprises a deleted or inactive PtsG gene. Deleted means that the coding sequence for PtsG is eliminated from the microorganism. Inactive means that the activity of the protein encoded by the gene has less than about 25%, 10%, 5%, or 1% of the wild-type protein. Alternatively, inactive means that the expression of the gene is reduced by about 75%, 90%, 95%, 99% or more as compared to the wild-type gene. In another embodiment of the invention, one or more microorganisms can perform one or more steps of the arabinose to xylitol pathway, while one or more other microorganisms can perform the remaining steps of the pathway wherein an end-product of xylitol is produced. Optionally, a mixture of microorganisms that can perform one or more steps of the pathway are used.

Vectors used in practicing the present invention are selected to be operable as cloning vectors or expression vectors in the selected host cell. Numerous vectors are known to practitioners skilled in the art, and selection of an appropriate vector and host cell is a matter of choice. The vectors may, for example, be bacteriophage, plasmids, viruses, or hybrids thereof, such as those described in Maniatis et al. [Molecular Cloning: A Laboratory Manual, Cold Springs Harbor Laboratory, 1989] or Ausubel et al. [Current Protocols in Molecular Biology, John Wiley & Sons, Inc, 1995], the contents of each of which are herein incorporated by reference. Further, the vectors may be non-fusion vectors (i.e., those producing the enzymes of the invention not fused to any heterologous polypeptide), or alternatively, fusion vectors (i.e., those producing the enzymes fused to a vector encoded polypeptide). The fusion proteins would of course vary with the particular vector chosen.

Within each specific vector, various sites may be selected for insertion of the isolated DNA sequences. These sites are usually designated by the restriction enzyme or endonuclease that cuts them.

The particular site chosen for insertion of the selected DNA fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those of skill in the art. None of these factors alone absolutely controls the choice of insertion site for a particular polypeptide. Rather, the site chosen reflects a balance of these factors, and not all sites may be equally effective for a given protein.

The nucleotide sequences comprising the L-xylulose reductase, D-tagatose 3-epimerase, and L-arabinose isomerase genes may be inserted into the desired vector by known techniques. If, however, the vector is to serve as an expression vector, the vector should have a promoter, and the DNA sequences should be inserted in the vector downstream of the promoter and operationally associated therewith (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be inserted. The vector should contain a terminator with necessary 3' untranslated sequences for RNA termination, stability, and/or poly(A) tail addition (if eucaryotic). Alternatively, any or all of the above control sequences may be ligated to the coding sequence prior to insertion into the vector.

DNA constructs may be introduced into the appropriate host by numerous methods described in the technical and scientific literature. Transformation of bacteria or yeast may be performed using standard techniques described in Maniatis et al., supra. Techniques for transforming filamentous fungi may include those described by Goosen et al. [Handbook for Applied Mycology, Arora, Elander & Mukerji, eds. (1992) pp. 151-195] and May et al. [Applied Molecular Genetics of Filamentous Fungi, Kinghorn and Turner, eds. (1992) pp. 1-27]. Transformations with *E. coli* are described in Example 2.

In general, linear or circular DNA constructs may be introduced into the host by techniques utilizing protoplast fusion, polyethylene glycol, liposomes, lithium acetate, electroporation, physical damage, biolistic bombardment, or *Agrobacterium* mediated transformation.

Successful transformants may be isolated by using markers, contained on the expression vectors, which confer a selectable trait to the transformed host. These may include nutritional selection related to substrate utilization (such as, growth on acetamide containing medium) or prototrophy of a required growth product (such as, arginine, leucine, or uracil). Dominant selectable markers (such as, resistance to ampicillin, G418, hygromycin, and phleomycin) are also useful in selecting transformants that have taken up the introduced DNA construct.

The DNA construct may be replicated autonomously or integrated into the genome of the host. Integration typically occurs by homologous recombination (for example, arginine selectable marker integrating in the chromosomal arginine gene) or at a chromosomal site unrelated to any genes on the DNA construct. Integration may occur by either a single or double cross-over event. It is also possible to have any number of these integration and replication types occurring in the same transformant.

The recombinant microorganisms of this invention are effective for the fermentation of L-arabinose to xylitol using conventional fermentation techniques. Production of xylitol is effected by contacting the above-mentioned recombinant microorganisms transformed with heterologous polynucleotide sequences coding for each of L-xylulose reductase, D-tagatose 3-epimerase, and L-arabinose isomerase, with a substrate comprising arabinose under conditions effective to produce xylitol from arabinose. The particular conditions selected will vary with the specific host microorganism. Without being limited thereto, in the preferred embodiment using transformed E. coli, the fermentation may be conducted using the L-arabinose containing substrate suspended in an aqueous medium, under aerobic conditions at a temperature of about 30 to 37° C. at approximately neutral pH with agitation. Substrates for use in the fermentation include L-arabinose or any L-arabinose containing material, and preferably hemicellulosic hydrolyzates. Examples of substrates include xylan hydrolysate and hemicellulose hydrolysate. Hydrolysis of the hemicellulosic materials may be accomplished using conventional techniques. A number of processes have been described for the enzymatic hydrolysis of lignocellulosic materials generally using cellulolytic and/or xylanolytic (hemicellulase) enzymes, and are suitable for use with the enzymes described herein as well. These include, but are not limited to, techniques described by Respell et al. (1997, Appl. Biochem. Biotechnol., 62:87-97), and techniques reviewed by Wright (1988, Chem. Engin. Progress, 84(8):62-74), the contents of each of which are incorporated by reference herein. Without being limited thereto, agricultural residues that can be used in the fermentation include, for example, grasses, bagasse residue, corn cob residue, flax straw residue, wheat straw residue, oat hull residue, or hydrolyzates of any of the above, as well as tree hydrolyzates, or a combination thereof.

The following examples are intended only to further illustrate the invention and are not intended to limit the scope of the invention which is defined by the claims.

Example 1

Cloning of the *Ambrosiozyma monospora* L-Xylulose Reductase Gene (alx1), the *Rhizobium radiobacter* D-Tagatose 3-Epimerase Gene (rdte) and *Escherichia coli* L-Arabinose Isomerase Gene (araA) and Construction of an L-Arabinose Isomerase/D-Tagatose 3-Epimerase/L-Xylulose Reductase Operon (araA/rdte/alx1)

Figure 2:
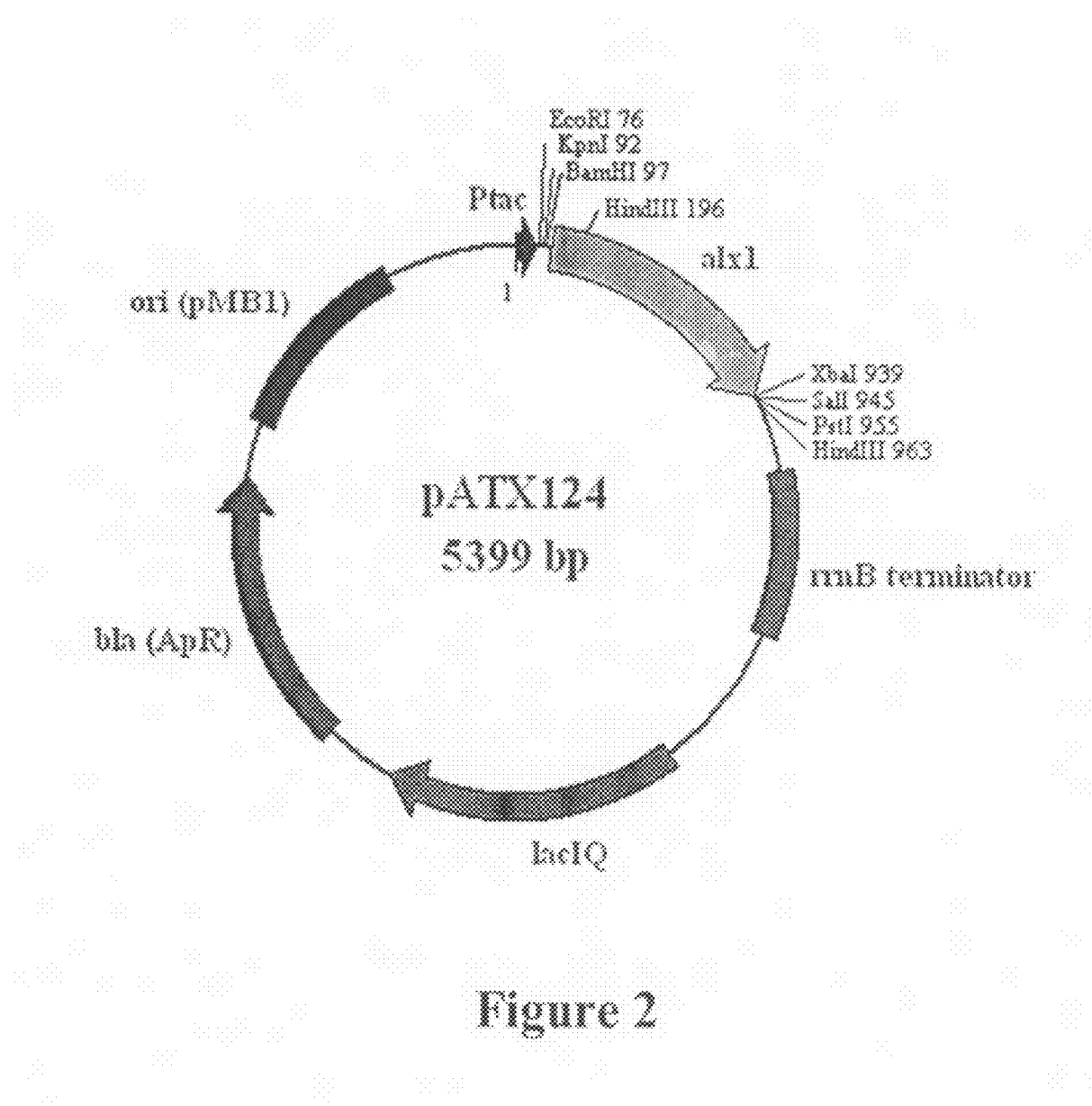
FIG. 2 shows the *A. monospora* L-xylulose reductase cloned into vector pTTQ18.

The *A. monospora* L-xylulose reductase gene (alx1) was cloned by RT-PCR using primers designed from the published sequence (GenBank Acc. No. AJ583159, SEQ ID No. 17) (Verho, 2004, ibid). *A. monospora* NRRL Y-1484 was grown overnight on YM medium containing 2% (w/v) L-arabinose. Total RNA was isolated using the RNeasy kit (Qiagen, Valencia, Calif., USA). The gene was amplified using the specific primers (Table 1, SEQ ID Nos. 1 and 2) and the One-Step RT-PCR Kit (Qiagen, Valencia, Calif., USA) with a DNA Engine Peltier Thermal Cycler PCR machine (BioRad, Hercules, Calif., USA), using standard amplification parameters. The RT-PCR reaction yielded a single band by gel electrophoresis. The gene was restricted with BamHI and XbaI using standard conditions and then ligated using the Quick Ligation Kit (New England Biolabs, Ipswich, Mass., USA) into an expression plasmid, pTTQ18 (Stark, 1987, Gene 51:255-267), restricted with the same enzymes to yield pATX124 (FIG. 2).

Figure 3:
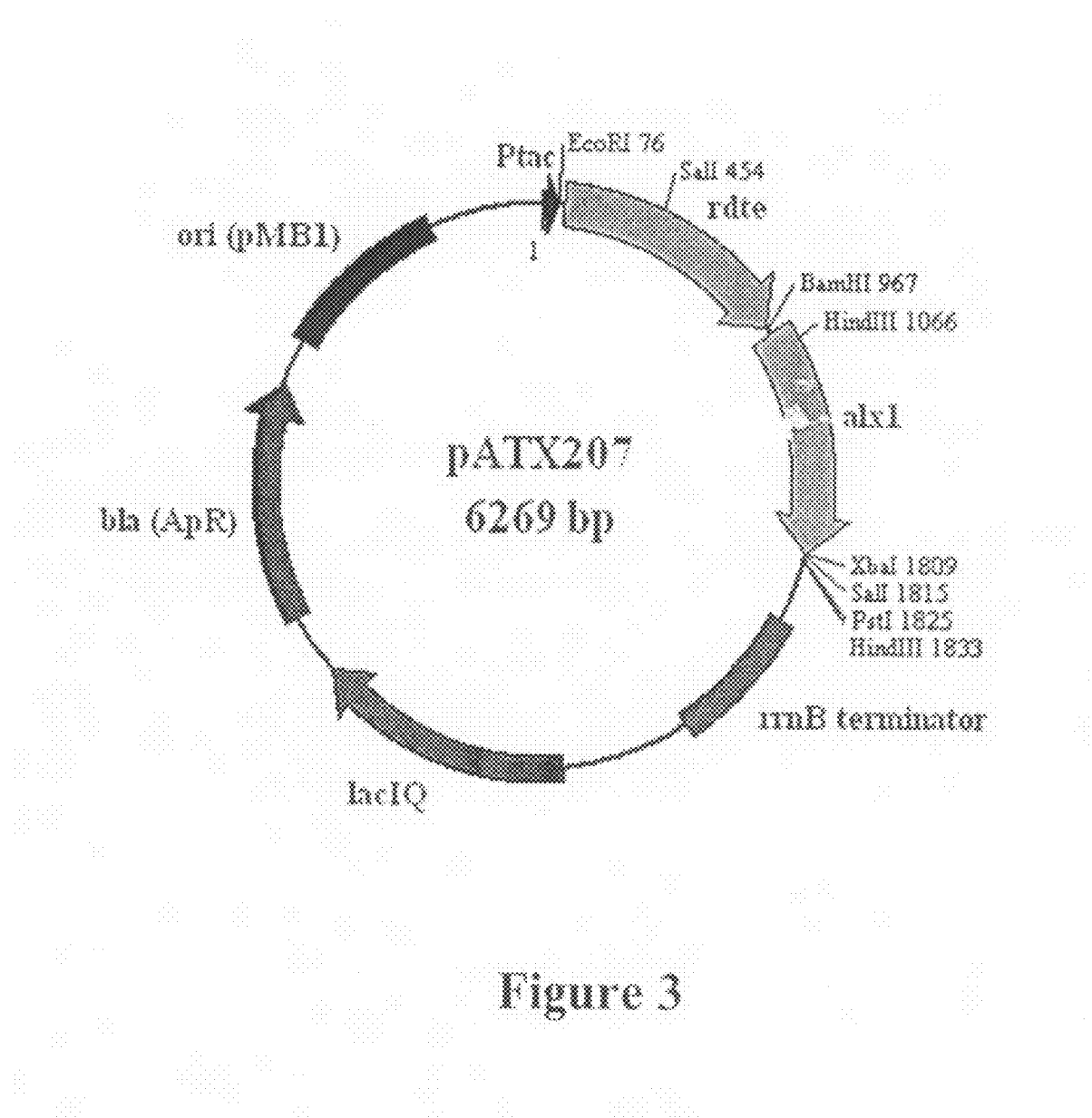
FIG. 3 shows the *A. monospora* L-xylulose reductase and *R. radiobacter* D-tagatose 3-epimerase cloned into vector pTTQ18.

A homologous sequence to the *Pseudomonas cichorii* D-tagatose 3-epimerase gene (Ishida, 1997, ibid) was found in a genomic sequence of *R. radiobacter* (GenBank Acc. No. AE008210, SEQ ID No. 15) by the BLAST sequence homology search. The *R. radiobacter* D-tagatose 3-epimerase gene (rdte) was amplified from genomic DNA purchased from ATCC (ATCC No. 33970D) using specific primers (Table 1, SEQ ID Nos. 3 and 4) and a taq DNA polymerase (Qiagen, Valencia, Calif., USA) with the DNA Engine Peltier Thermal Cycler PCR machine (BioRad, Hercules, Calif., USA), using standard amplification parameters. The PCR reaction yielded a single band by gel electrophoresis. The gene was restricted with EcoRI and BamHI using standard conditions and then ligated using the Quick Ligation Kit (New England Biolabs, Ipswich, Mass., USA) into pATX124 restricted with the same enzymes to yield pATX207 (FIG. 3).

Figure 4:
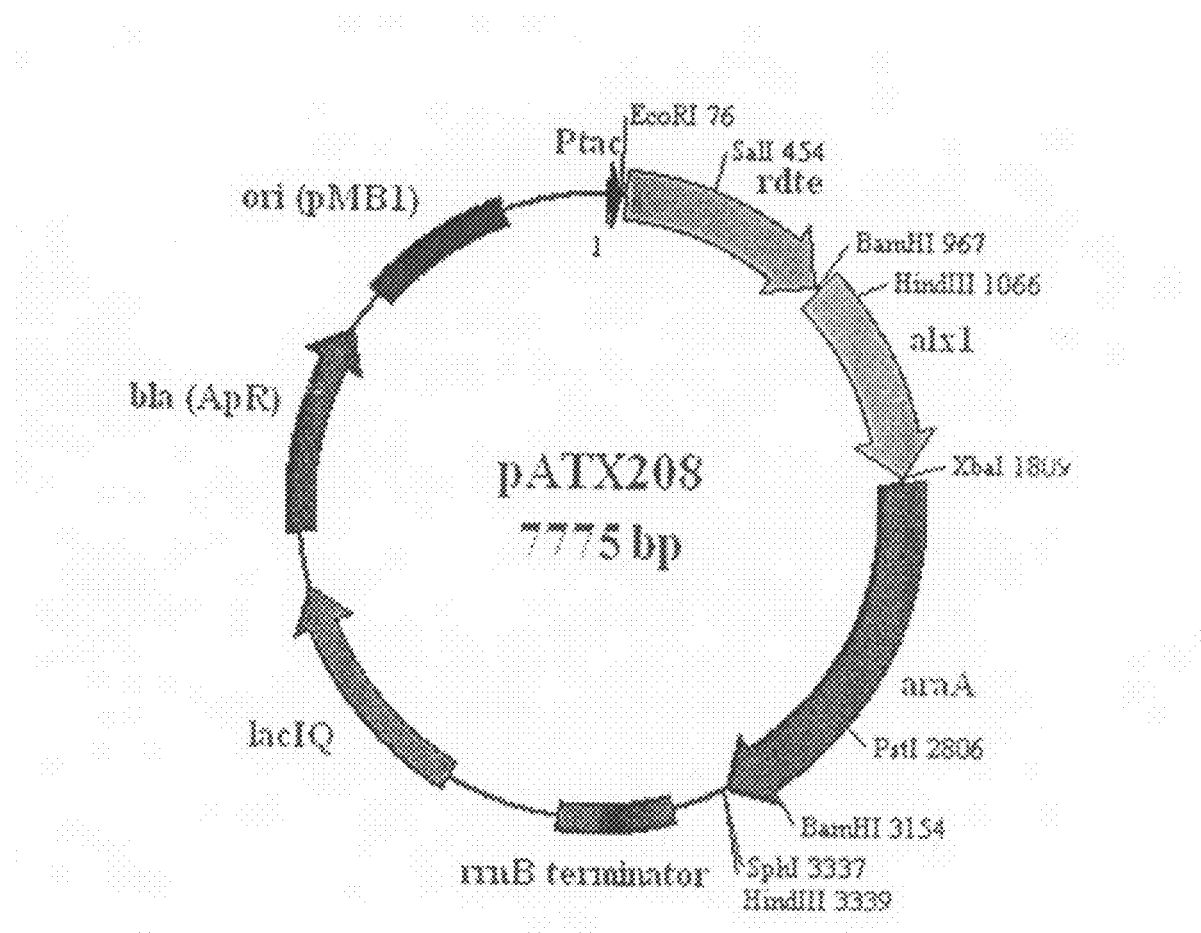
FIG. 4 shows the araA/rdte/alx1 operon cloned into vector pTTQ18.

The *E. coli* L-arabinose isomerase gene (araA) was cloned by PCR using primers designed from the published sequence (GenBank Acc. No. M15263, SEQ ID No. 13) (Lee, 1986, ibid). *E. coli* strain AB707 was grown overnight on the Luria-Bertani (LB) medium and then the genomic DNA was isolated using the Genomic-tip 100/G (Qiagen, Valencia, Calif., USA). The gene was amplified using the specific primers (Table 1, SEQ ID Nos. 5 and 6) and the taq DNA polymerase (Qiagen, Valencia, Calif., USA) with the DNA Engine Peltier Thermal Cycler PCR machine (BioRad, Hercules, Calif., USA), using standard amplification parameters. The PCR reaction yielded a single band by gel electrophoresis. The gene was restricted with XbaI and SphI using standard conditions and then ligated using the Quick Ligation Kit (New England Biolabs, Ipswich, Mass., USA) into plasmid pATX207 restricted with the same enzymes to yield pATX208 (FIG. 4).

DNA sequencing using the BigDyeTerminator v3.1 Cycle Sequencing Kit and the ABI PRISM 3100 Genetic Analyzer (Applied Biosystems, Foster City, Calif., USA) showed the cloned sequences were identical to those of the published genes.

Example 2

Xylitol Synthesis from L-Arabinose Using the araA/rdte/alx1 Operon

To test the activity of the araA/rdte/alx1 operon, plasmid pATX208 was transformed into *E. coli* strain BW25113' (Datsenko, 2000) by electroporation (BW25113/pATX208). The strain was inoculated from a single colony into 3 ml LB medium supplemented with 200 mg $l^{-1}$ ampicillin and incubated overnight at 30° C. with shaking (250 rpm). An aliquot of the overnight culture was diluted 100-fold into 20 ml of fresh LB medium containing 1% (w/v) L-arabinose and 200 mg $l^{-1}$ ampicillin and incubated (30'C, 250 rpm) for 2 hours. To induce transcription of the operon under control of the tac promoter, isopropyl-β-D-thiogalactopyranoside (IPTG, 1 mM) was added to the cultures. The cultures were further incubated at 30° C. with shaking (250 rpm) and aliquots were removed at various time points after the IPTG induction. The strain carrying pTTQ18 (vector only) was used as a negative control. The samples were monitored for xylitol formation from L-arabinose by HPLC analysis using an Aminex HPX-87P column (BioRad, Hercules, Calif., USA). After 24 hours post induction, strain BW25113/pATX208 displayed a 24% conversion of L-arabinose to xylitol, showing the strain successively synthesizes xylitol from L-arabinose (Table 3).

Example 3

Figure 5:
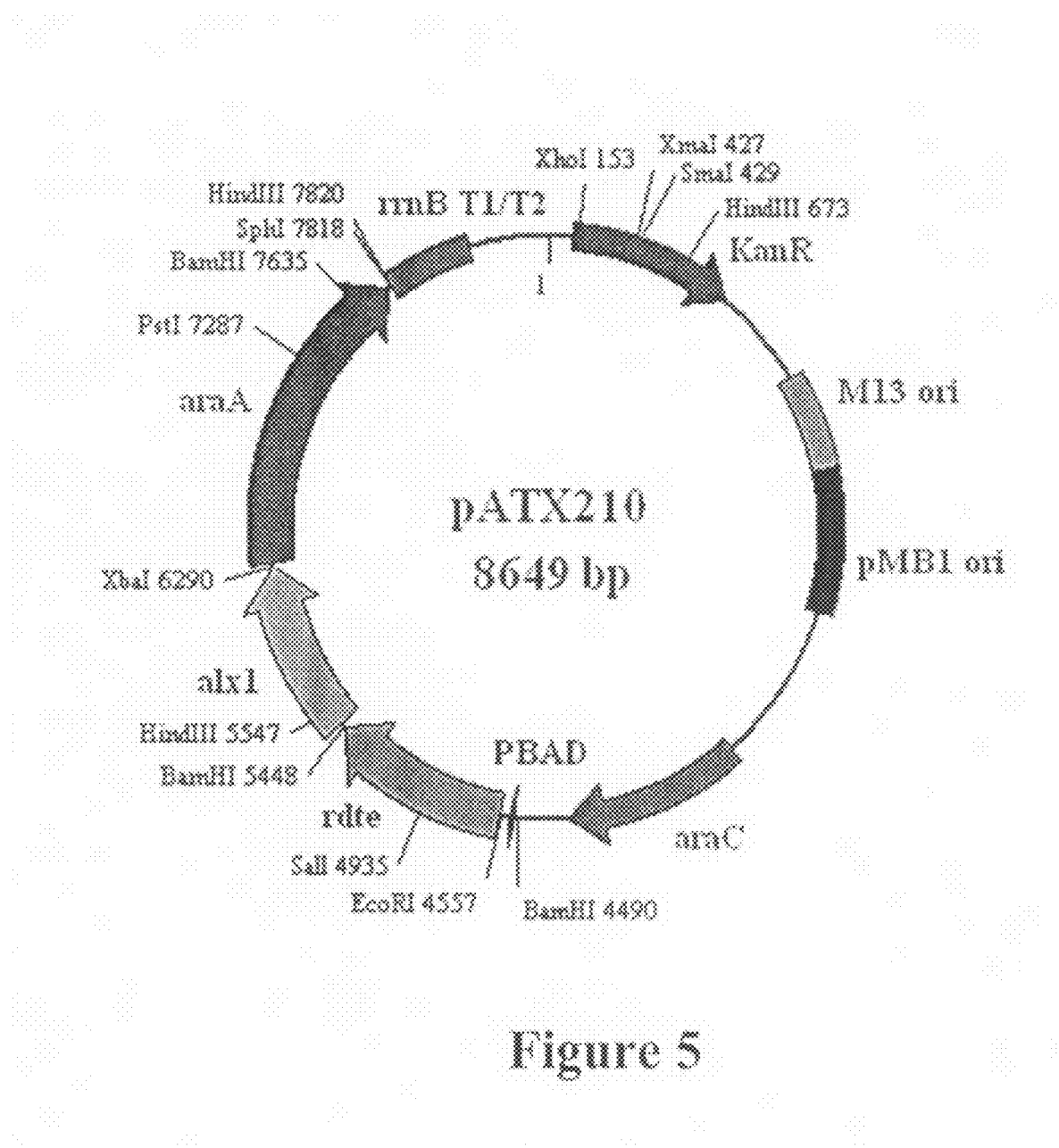
FIG. 5 shows the araA/rdte/alx1 operon cloned into vector pBAD18-Kan.

Construction of the L-Arabinose Isomerase/D-Tagaotose 3-Epimerase/L-Xylulose Reductase (araA/rdte/alx1) Operon Driven by the araBAD Promoter ($P_{BAD}$) and Xylitol Synthesis from L-Arabinose Using the $P_{BAD}$-araA/rdte/alx1 Operon Plasmid pATX208 was digested with restriction enzymes EcoRI and SphI using standard conditions. The digested plasmid DNA was loaded onto an agarose gel and then a 3.3-kb DNA fragment containing the araA/rdte/alx1 operon was extracted and purified from the gel using the QIAquick Gel Extraction Kit (Qiagen, Valencia, Calif., USA). The extracted DNA fragment was ligated using the Quick Ligation Kit into an expression plasmid, pBAD18-Kan (Guzman et al., 1995, J. Bacteriol. 177: 4121-4130), restricted with the same enzymes to yield pATX210 (FIG. 5).

To test the expression and activity of the araA/rdte/alx1 operon under control of the araBAD promoter ($P_{BAD}$) plasmid pATX210 was transformed into strain BW25113 by electroporation (BW25113/pATX210). The strain was inoculated from a single colony into 3 ml LB medium supplemented with 50 mg $l^{-1}$ kanamycin and incubated overnight at 30° C. with shaking (250 rpm). An aliquot of the overnight culture was diluted 100-fold into 20 ml of fresh LB medium containing 1% (w/v) L-arabinose and 50 mg $l^{-1}$ kanamycin. The culture was further incubated at 30° C. with shaking (250 rpm) and aliquots were removed at various time points after the inoculation. The samples were monitored for xylitol formation from L-arabinose by HPLC analysis using the Aminex HPX-87P column (BioRad, Hercules, Calif., USA). After 24-h culture, strain BW25113/pATX210 displayed a 25% conversion of L-arabinose to xylitol, showing expression of the araA/rdte/alx1 operon is induced by L-arabinose included in the medium as the conversion substrate without any additional inducers (Table 4).

Example 4

Cloning and Analysis of L-Xylulose Reductase Gene (plxr) from *Pantoea ananatis*

*P. ananatis* has been reported to produce L-xylulose reductase (xylitol 4-dehydrogenase) by growing on xylitol (Doten, 1985). *P. ananatis* NRRL B-14773 was incubated at 25° C. on a minimal salt agar supplemented with 0.5% xylitol to isolate xylitol-utilizing mutants (Oliver et al., 1969, Anal. Biochem. 27:300-305; Doten and Mortlock, 1985, J. Bacteriol. 161: 529-533). Xylitol-utilizing colonies were appeared after 3 weeks of incubation by spontaneous mutations. Xylitol-negative mutants were then isolated from these xylitol-utilizing mutants by random gene disruption using the EZ-TN [R6Kγori/KAN-2] Tnp transposome Kit (Epicentre, Madison, Wis., USA). One ml of overnight culture of the xylitol-utilizing strain was inoculated into 100 ml LB medium and incubated at 30° C. The culture was allowed to grow to a density of $OD_{600}=0.9$, placed on ice for 10 min and then transferred into centrifuge bottles. The cells were washed three times with 10% glycerol and resuspended after final centrifugation in a volume of 500 µl. One 41 each of the EZ-TN [R6Kγori/KAN-2] Tnp Transposome and the Type-One Restriction Inhibitor (Epicentre, Madison, Wis., USA) was added to 40 µl of the cell suspension. The cell-transposome mixture was stored on ice for 1 min, transferred to a 1 mm-wide cuvette, and subjected to a pulse from a Gene Pulser electroporater (BioRad, Hercules, Calif., USA). The settings of the electroporation were 1.8 kV, 25 µF and 200Ω, which resulted in a pulse time of 4.0 ms. The cells were suspended in 1 ml SOC medium and allowed to recover for 1 hour at 30° C. with shaking. One hundred 41-aliquots of the electroporated cells were plated onto MacConkey agar (BD Diagnostic Systems, Sparks, Md., USA) supplemented with 1% xylitol and 50 mg $l^{-1}$ kanamycin and incubated at 30° C. for 48 hours. White or pale pink colonies are selected as xylitol-negative mutants and restreak onto fresh xylitol MacConkey agar supplemented with 1% xylitol and 50 mg $l^{-1}$ kanamycin to isolate single colonies.

Xylitol dehydrogenase activities of the xylitol-negative mutants were evaluated to isolate mutants that lack the xylitol dehydrogenase activity (xylitol dehydrogenase mutant). Cells of the mutants were incubated in LB medium for 20 hours with shaking (250 rpm) and harvested from a 1-ml aliquot of each culture by centrifugation. Soluble cell fractions were prepared using 50 µl of the BugBuster Protein Extraction Reagent (Novagen, Darmstadt, Germany) containing 0.2% (v/v) Lysonase Bioprocessing Reagent (Novagen, Darmstadt, Germany) according to a supplier's manual. To assay xylitol dehydrogenase activity, 10 µl of each cell lysate was mixed with 990-µl reaction mixture (100 mM Tris-Cl (pH9.0), 0.5 mM $MgCl_2$, 2 mM NAD and 100 mM xylitol) in a quartz cuvette at 30° C. Activity was measured by following the increase in absorbance at 340 nm using a spectrophotometer (model 8453, Agilent, USA). The activities varied among the mutants and one mutant showed no xylitol dehydrogenase activity.

To isolate the gene disrupted by the transposon insertion, genomic DNA was isolated from the xylitol dehydrogenase mutant using the Genomic Tip 100/G (Qiagen, Valencia, Calif., USA). One microgram of the genomic DNA was fragmented by EcoRI digestion and then self-ligated using 2 U of T4 DNA ligase in 20 µl of reaction for 1 hour at room temperature. *E. coli* BW25141 was transformed with 1 µl of the ligation reaction and incubated on LB agar containing 50 mg $l^{-1}$ kanamycin, allowing only the cells carrying the genomic DNA transposed with the EZ-TN(R6Kγori/KAN-2) to grow. The transposed DNA was isolated from kanamycin-resistant colonies using the Spin Doctor Molecular Biology Miniprep Kit (Gerard Biotech, Oxford, Ohio, USA). Nucleotide sequences of genomic DNA flanking the transposon were analyzed using the transposon-specific primers (Epicentre, Madison, Wis., USA), the BigDyeTerminator Cycle Sequencing Kit and the ABI PRISM 3100 Genetic Analyzer. (Applied Biosystems, Foster City, Calif., USA), showing the transposon was inserted into a gene (plxr) that exhibits sequence similarity to oxidoreductases belonging to the short chain dehydrogenase/reductase family.

Figure 6:
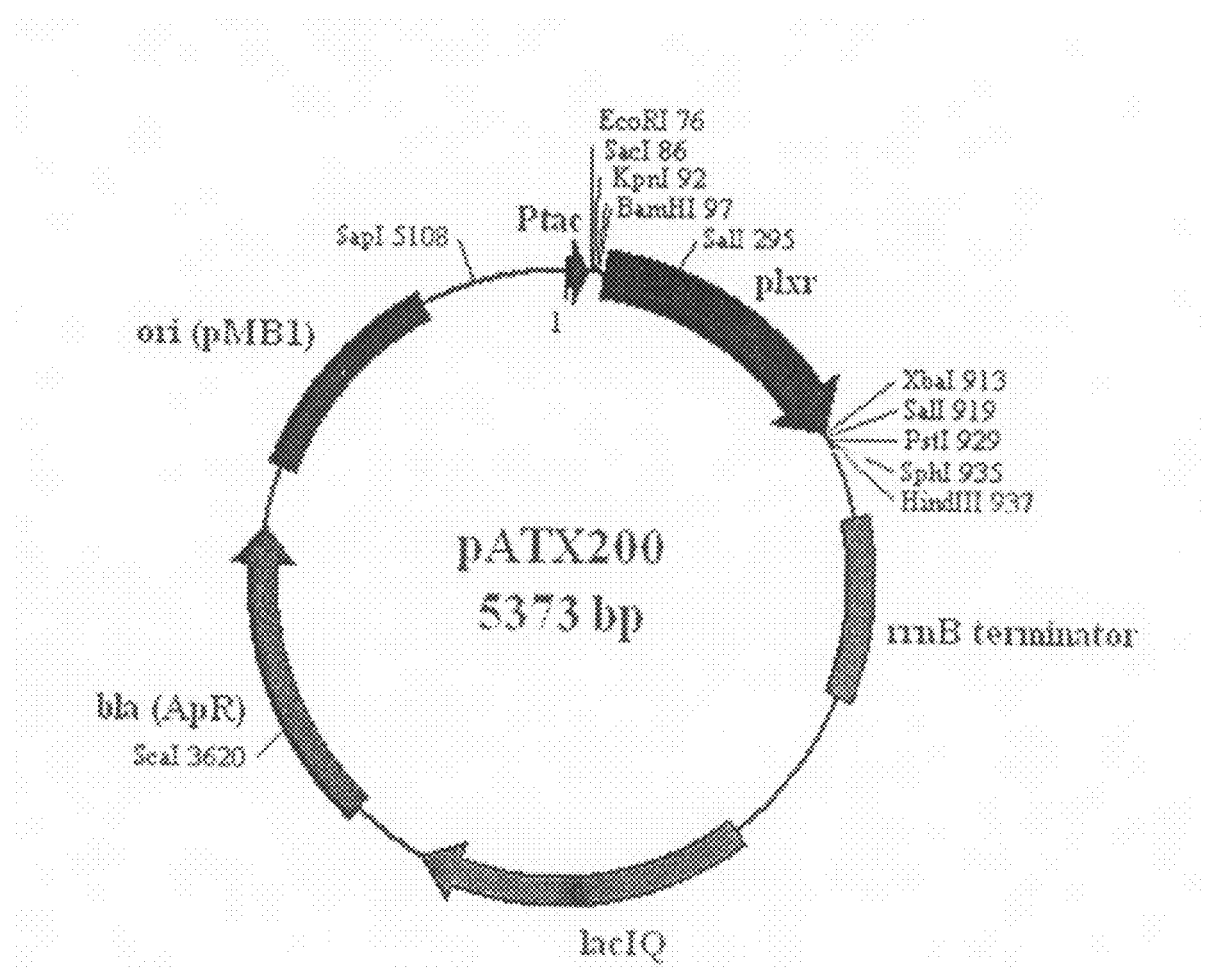
FIG. 6 shows the *Pantoea ananatis* L-xylulose reductase (plxr) cloned into vector pTTQ18.

To test the enzyme activity, the plxr gene was amplified from genomic DNA of *P. ananatis* NRRL B-14773 using specific primers (Table 1, SEQ ID Nos. 7 and 8) and the PfuUltra Hotstart High-Fidelity DNA Polymerase (Stratagene, La Jolla, Calif., USA) with the DNA Engine Peltier Thermal Cycler PCR machine (BioRad, Hercules, Calif., USA), using standard amplification parameters. The PCR reaction yielded a single band by gel electrophoresis. The gene was restricted with BamHI and XbaI using standard conditions and then ligated using the Quick Ligation Kit (New England Biolabs, Ipswich, Mass., USA) into the expression, plasmid pTTQ18 restricted with the same enzymes to yield pATX200 (FIG. 6). Then, the pATX200 plasmid was transformed into *E. coli* strain AB707 by electroporation (AB707/pATX200). The strain was inoculated from a single colony into 3 ml LB medium supplemented with 200 mg $l^{-1}$ ampicillin and incubated overnight at 30° C. with shaking (250 rpm). An aliquot of the overnight culture was diluted 100-fold into 20 ml of fresh LB medium containing 1% (w/v) xylitol and 200 mg $l^{-1}$ ampicillin and incubated (37° C., 250 rpm) for 2 hours. To induce transcription of the gene, 1 mM IPTG was added to the cultures. The cultures were further incubated at 37° C. with shaking (250 rpm) and aliquots were removed at various time points after the IPTG induction. The strain carrying pTTQ18 (AB707/pTTQ18) was used as a negative control. The samples were monitored for L-xylulose formation from xylitol by HPLC analysis using the Aminex HPX-87P column (BioRad, Hercules, Calif., USA). After 24 hours post induction, strain AB707/pATX200 displayed a 31% conversion of xylitol to xylulose (Table 5). The isomeric form of the xylulose formed was determined by measuring the optical rotation of the culture with a polarimeter (model 341, Perkin-Elmer, Wellesley, Mass., USA). The optical rotation of the 24-h culture was 0.107°, whereas that of the same concentration of authentic D-xylulose (0.3% in LB medium; Sigma-Aldrich, St. Louis, Mo., USA) was −0.114. These results indicate that Plxr has the xylitol 4-dehydrogenase/L-xylulose reductase activity. As expected the control culture did not accumulate any xylulose (Table 5).

Example 5

Construction of the L-Arabinose Isomerase/D-Tagaotose 3-Epimerase/*P. ananatis* L-Xylulose Reductase Operon (araA/rdte/plxr)

Figure 7:
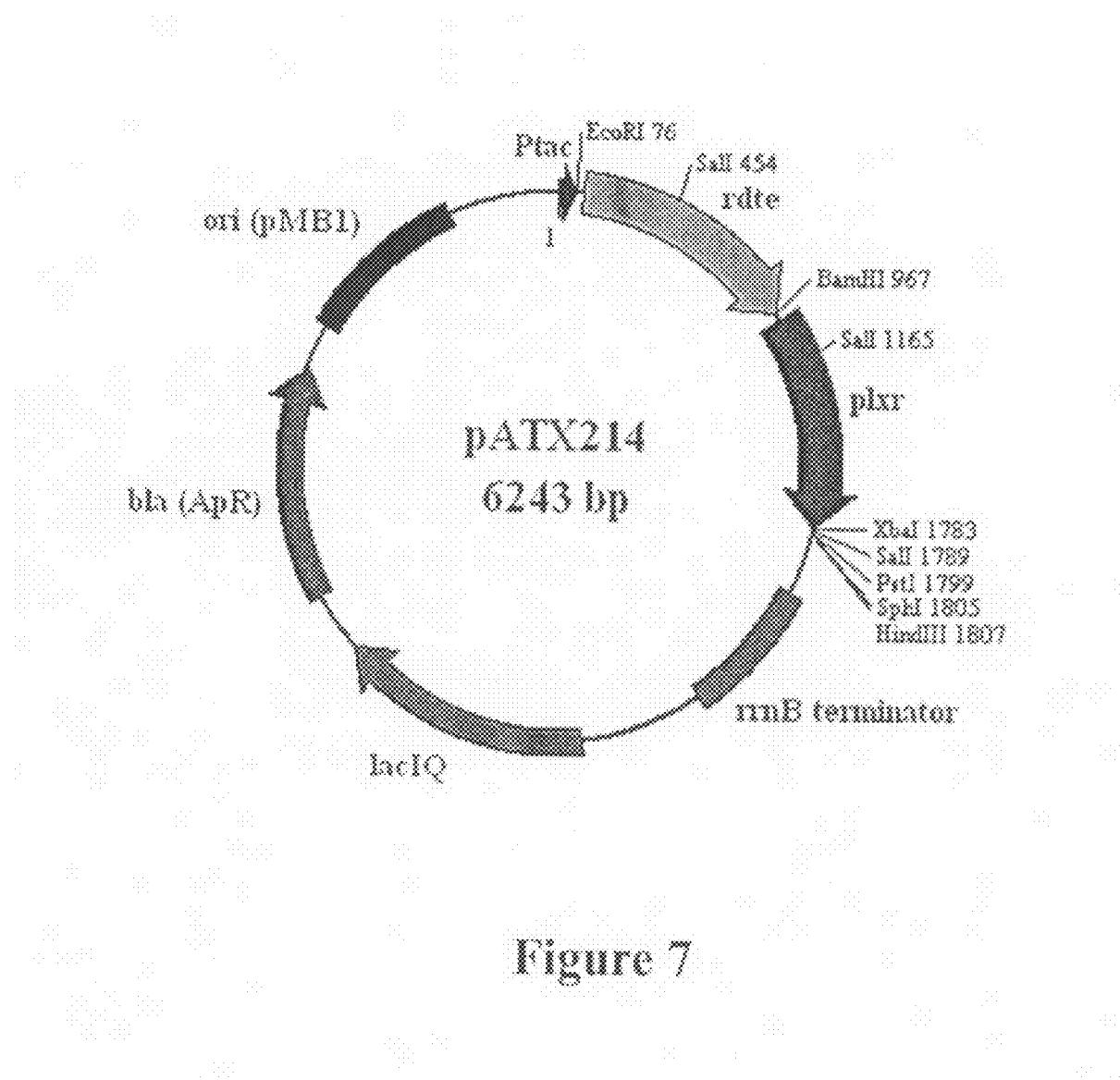
FIG. 7 shows the *P. ananatis* L-xylulose reductase and *R. radiobacter* D-tagatose 3-epimerase cloned into vector pTTQ18.
Figure 8:
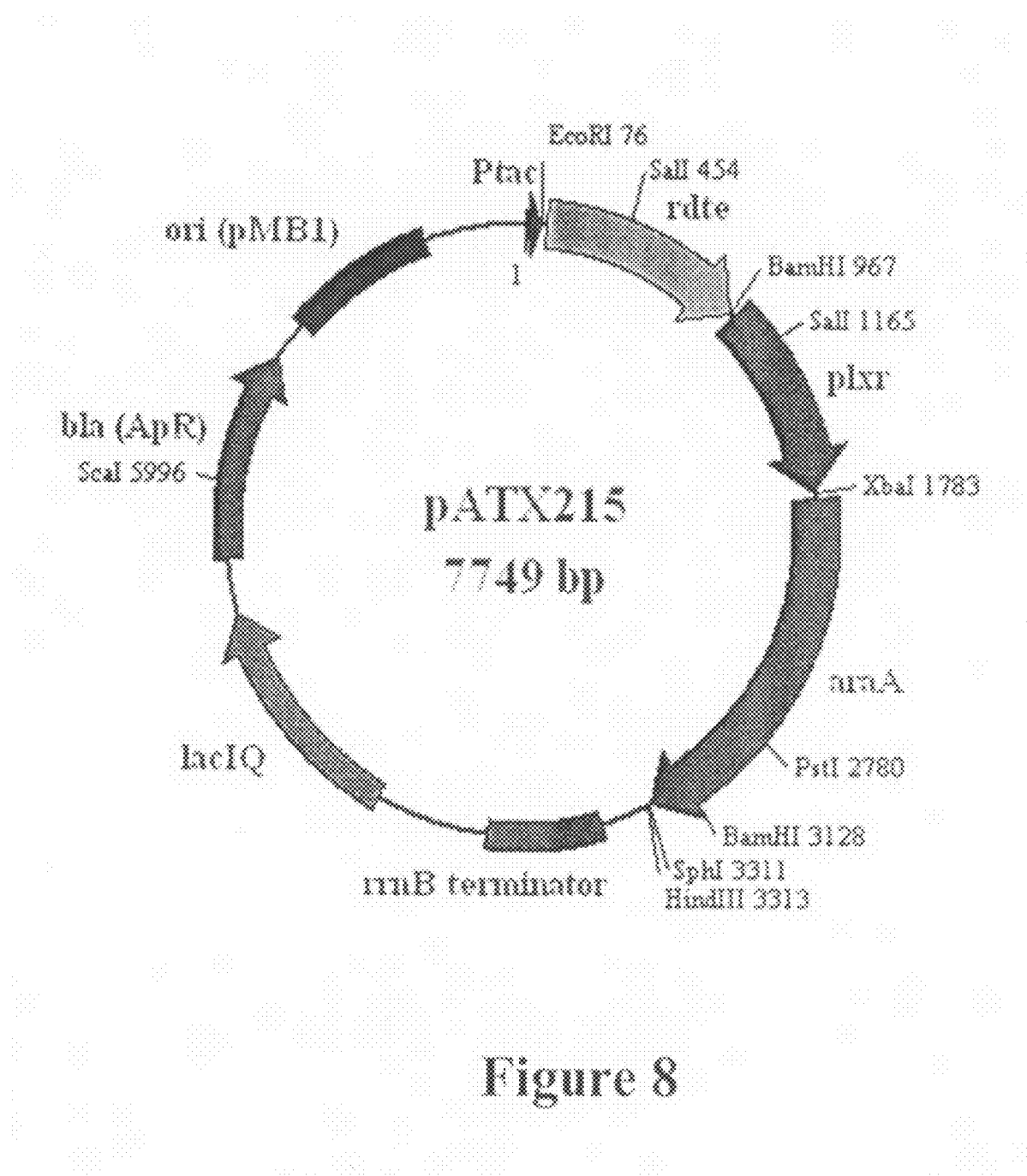
FIG. 8 shows the araA/rdte/plxr operon cloned into vector pTTQ18.
Figure 9:
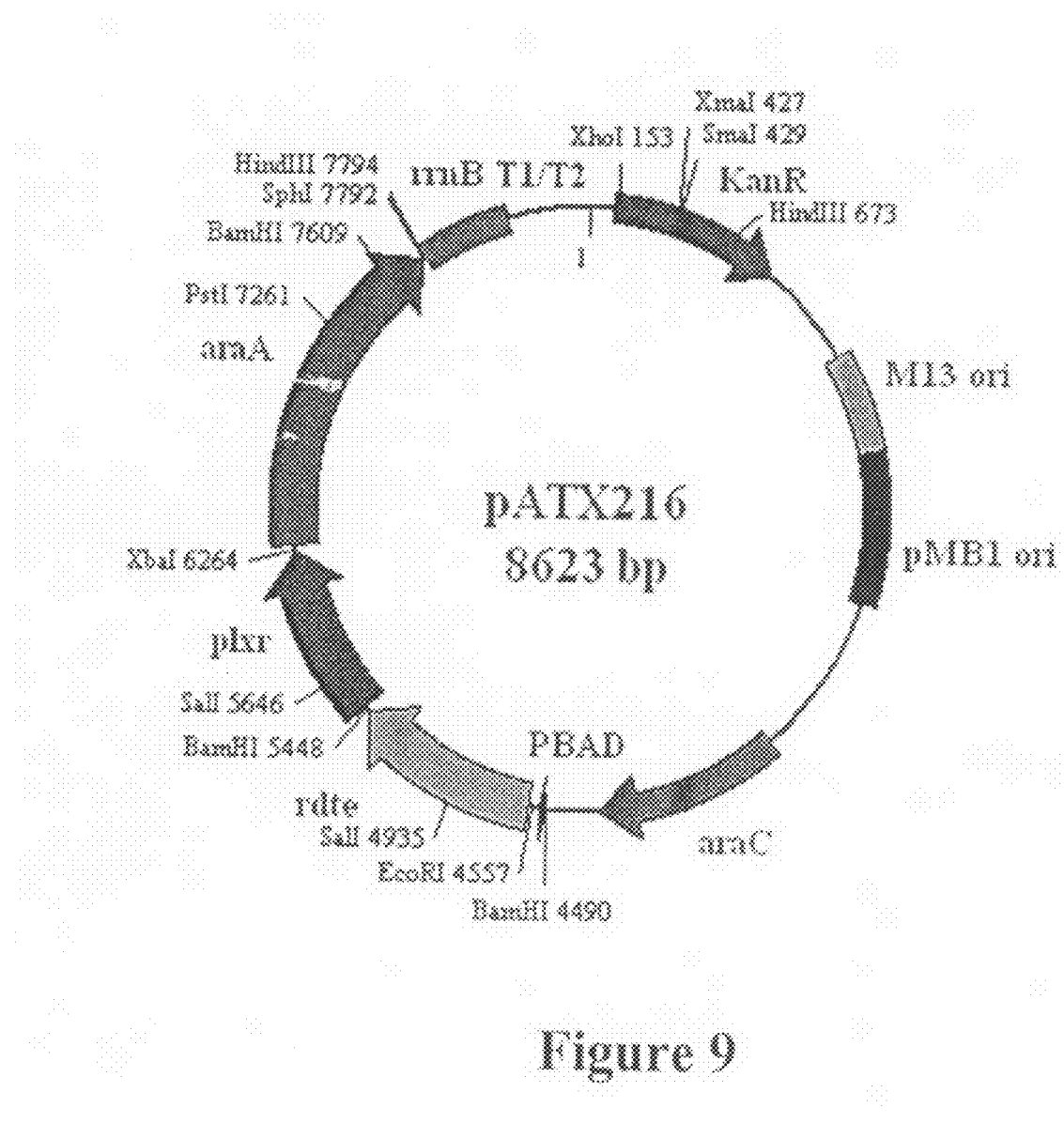
FIG. 9 shows the araA/rdte/plxr operon cloned into vector pBAD18-Kan.

Plasmid pATX200 was digested with BamHI and XbaI using standard conditions. The digested plasmid was loaded onto an agarose gel and then a 0.8-kb DNA fragment containing the plxr gene was extracted and purified from the gel using the QIAquick Gel Extraction Kit (Qiagen, Valencia, Calif., USA). The purified DNA fragment was ligated using the Quick Ligation Kit into plasmid pATX207 restricted with the same enzymes to yield pATX214 (FIG. 7). To prepare the AraA gene, plasmid pATX208 was digested with XbaI and SphI using standard conditions and a 1.5-kb DNA fragment including the AraA gene was extracted and purified from an agarose gel as described above. Then, the AraA gene was ligated using the Quick Ligation Kit (New England Biolabs, Ipswich, Mass., USA) into plasmid pATX214 restricted with the same enzymes to yield pATX215 (FIG. 8). The araA/rdte/plxr operon (3.3 kb) was isolated by restriction digestion of pATX215 with EcoRI and SphI and ligated into the expression plasmid pBAD18-Kan restricted with the same enzymes. The resultant plasmid was designated pATX216 (FIG. 9).

Example 6

Construction and Analysis of the *E. coli* L-Xylulokinase Mutant (ZUC99)

The xylitol synthesis pathway developed converts L-arabinose to xylitol through L-ribulose and L-xylulose as intermediates. *E. coli* strain BW25113 lacks the L-arabinose catabolic pathway including ribulokinase (AraB) that phosphorylates L-ribulose to L-ribulose 5-phosphate. However, *E. coli* BW25113 still possesses the L-xylulokinase (LyxK), which has been reported to catalyze the first step of the L-xylulose catabolism in *E. coli* (Badía et al., 1991, J. Bacteriol. 173:5144-5150; Sánchez et al., 1994, J. Biol. Chem. 269:29665-29669). In order to prevent degradation of xylitol through the L-xylulose catabolic pathway, the lyxK gene was disrupted using the method of Datsenko and Wanner (Datsenko, 2000, Proc. Natl. Acad. Sci. USA 70:84-87). The lyxK deletion was inserted into strain BW25113 using primers designed with homology either side of the lyxK gene (Table 1, SEQ ID Nos. 9 and 10) to yield strain ZUC75 (lyxK::kan, lacI$^q$, rrnB$_{T14}$, $\Delta$lacZ$_{WJ16}$, hsdR514, $\Delta$araBAD$_{AH33}$, $\Delta$rhaBAD$_{LD78}$). ZUC75 was then cured of the inserted kanamycin gene as per the published protocol to yield ZUC99 ($\Delta$lyxK, lacI$^q$, rrnB$_{T14}$, $\Delta$lacZ$_{WJ716}$, hsdR514, $\Delta$araBAD$_{AH33}$, $\Delta$rhaBAD$_{LD78}$).

To test the L-xylulose accumulation, the pATX200 plasmid was transformed into ZUC99 by electrdporation (ZUC99/pATX200). The strain was inoculated from a single colony into 3 ml LB medium supplemented with 200 mg l$^{-1}$ ampicillin and incubated overnight at 30° C. with shaking (250 rpm). An aliquot of the overnight culture was diluted 100-fold into 20 ml of fresh LB medium containing 1% (w/v) xylitol and 200 mg 1' ampicillin and incubated (37'C, 250 rpm) for 2 hours. To induce expression of the gene under control of the tac promoter, 1 mM IPTG was added to the cultures. The cultures were further incubated at 37° C. with shaking (250 rpm) and aliquots were removed at various time points after the IPTG induction. Strain AB707 carrying pATX200 (AB707/pATX200) was used as a control. The samples were monitored for L-xylulose formation from xylitol by HPLC analysis using the Aminex HPX-87P column (BioRad, Hercules, Calif., USA). After 24 hours post induction, strains ZUC99/pATX200 and AB707/pATX200 displayed 46% and 31% conversions of xylitol to L-xylulose, respectively (Table 6). After 72 hours post induction, ZUC99/pATX200 still synthesized and accumulated L-xylulose from xylitol (59% conversion), whereas no L-xylulose or xylitol was detected in the culture of AB707/pATX200 (Table 6). These results show the L-xylulokinase mutant, ZUC99 is highly effective in preventing xylitol degradation through the L-xylulose catabolic pathway.

Example 7

Xylitol Synthesis from L-Arabinose Using the araA/rdte/alx1 Operon and the L-Xylulokinase Mutant (ZUC99)

To test the xylitol synthesis from L-arabinose using strain ZUC99, plasmid pATX210 was transformed into ZUC99 by electroporation (ZUC99/pATX210). The strain was inoculated from a single colony into 3 ml LB medium supplemented with 50 mg l$^{-1}$ kanamycin and incubated overnight at 30° C. with shaking (250 rpm). An aliquot of the overnight culture was diluted 100-fold into 20 ml of fresh LB medium containing 1% (w/v) L-arabinose and 50 mg 1–1 kanamycin. The culture was incubated at 30° C. with shaking (250 rpm) and aliquots were removed at various time points after the inoculation. The samples were monitored for xylitol formation from L-arabinose by HPLC analysis using the Aminex HPX-87P column (BioRad, Hercules, Calif., USA). After 24-h culture, strain ZUC99/pATX210 displayed a 30% conversion of L-arabinose to xylitol, showing the strain successively synthesizes xylitol from L-arabinose (Table 7).

Example 8

Xylitol Synthesis from L-Arabinose Using the araA/rdte/plxr Operon and the L-Xylulokinase Mutant (ZUC99)

To test the xylitol synthesis using the araA/rdte/plxr operon, plasmid pATX216 were inserted into strain ZUC99 by electroporation (ZUC99/pATX216). The strains were inoculated from a single colony into 3 ml LB medium supplemented with 50 mg 1$^{-1}$ kanamycin and incubated overnight at 30° C. with shaking (250 rpm). After incubation, an aliquot of each culture was diluted 100-fold into 20 ml of fresh LB medium containing 1% (w/v) L-arabinose and 50 mg 1$^{-1}$ kanamycin. The cultures were incubated at 30° C. with shaking (250 rpm) and aliquots were removed at various time points after the inoculation. The samples were monitored for xylitol formation from L-arabinose by HPLC analysis using an Aminex HPX-87P column (BioRad, Hercules, Calif., USA). After 24-h culture, strains ZUC99/pATX216 displayed a 23% conversion of L-arabinose to xylitol, showing the strain successively synthesizes xylitol from L-arabinose (Table 8).

Example 9

Xylitol Synthesis from L-Arabinose using Glycerol as a Co-Substrate

To improve L-arabinose utilization for the xylitol synthesis, glycerol was added to the medium as a co-substrate. Strain ZUC99/pATX210 was inoculated from a single colony into 3 ml LB medium supplemented with 50 mg $l^{-1}$ kanamycin and incubated overnight at 30° C. with shaking (250 rpm). An aliquot of the overnight culture was diluted 100-fold into 20 ml of fresh LB medium containing 1% (w/v) L-arabinose, 1.5% (w/v) glycerol and 50 mg $l^{-1}$ kanamycin. The culture was incubated at 30° C. with shaking (250 rpm) and aliquots were removed at various time points. The samples were monitored for xylitol formation from L-arabinose by HPLC analysis using the Aminex HPX-87P column (BioRad, Hercules, Calif., USA). Strain ZUC99/pATX210 displayed 100% conversions of L-arabinose to xylitol after 24-h culture, showing the glycerol addition significantly improves xylitol yield (Table, 9). When the strain was cultured in the medium without glycerol, only 66% of the L-arabinose consumed was converted to xylitol after 24-h culture (Table 7), showing the glycerol addition prevents L-arabinose metabolism for energy and biomass in *E. coli* cells.

Example 10

Xylitol Synthesis from L-Arabinose using the *E. coli* Catabolite Repression Mutant (ZUC110)

When glucose is present, the xylitol synthesis from L-arabinose using strain ZUC99/pATX210 was completely inhibited due to the catabolite repression (Table 10). To avoid this glucose effect, a catabolite repression mutant was constructed by disruption of the gene (ptsG) encoding $IIBC^{Glc}$, of which the mutant was reported to co-metabolize glucose and L-arabinose (Hernández-Montalvo et al., 2001, Appl. Microbiol. Biotechnol. 57:186-191), one such strain is ZUC72 (ptsG21, ΔxylB see example 22 of copending U.S. patent application Ser. No. 11/133,045, published May 25, 2006 as US2006/0110809, the contents of which are incorporated by reference herein). To be useful for this example an arabinose operon deletion (ΔaraBAD) was inserted to prevent the catabolism of L-arabinose. The deletion was made in ZUC72 using primers designed to the flanking sequences of the araBAD operon (Table 1 SEQ ID Nos 11 and 12) to yield strain ZUC110 (ptsG21, ΔxylB, araBAD::cam) by the method of Datsenko and Wanner (Datsenko, 2000, ibid).

To test the xylitol synthesis from L-arabinose using strain ZUC110, plasmid pATX210 was transformed into strain ZUC110 by electroporation (ZUC110/pATX210). The strain was inoculated from a single colony into 3 ml LB medium supplemented with 50 mg $l^{-1}$ kanamycin and incubated overnight at 30° C. with shaking (250 rpm). An aliquot of the overnight culture was diluted 100-fold into 20 ml of fresh LB medium containing 1% (w/v) L-arabinose, 1% (w/v) glucose and 50 mg kanamycin. The culture was incubated at 30° C. with shaking (250 rpm) and aliquots were removed at various time points after the inoculation. The samples were monitored for xylitol formation from L-arabinose by HPLC analysis using the Aminex HPX-87P column (BioRad, Hercules, Calif., USA). After 24-h culture, ZUC99/pATX210 displayed a 60% conversion of L-arabinose to xylitol, showing the strain is able to synthesize xylitol from mixture of L-arabinose and glucose (Table 10).

It is understood that the foregoing detailed description is given merely by way of illustration and that modifications and variations may be made therein without departing from the spirit and scope of the invention.

TABLE 1

List of oligonucleotide PCR primers.

| Gene | Organism | Forward Primer (5' to 3') | Reverse Primer (5' to 3') |
| --- | --- | --- | --- |
| alx1 | A. monospora | SEQ ID No. 1, GCGGATCCATAAAGGAGGATATATAATGACTGACTACATTCC | SEQ ID No. 2, GCTCTAGACTACCAAGAAGTGAAACCACCATCAAC |
| rdte | R. radiobacter | SEQ ID No. 3, GCGAATTCTAAGGAGGATATATTATGAAACACGGCATCT | SEQ ID No. 4, GCGGATCCTCAGCCACCAAGAAC |
| araA | E. coli | SEQ ID No. 5, GCGTCTAGATAAGGAGGATCATCTATGACGATTTTTGATAA | SEQ ID No. 6, GGCATGCTTAGCGACGAAACCCGTAATA |
| plxr | P. ananatis | SEQ ID No. 7, CGGATCCTTAGGAGGATATATTATGAGCGGTGAATAT | SEQ ID No. 8, GCTCTAGATTACCAGATGGTAAAGCCACC |
| Lyxk (flanking homology) | E. coli | SEQ ID No. 9 GATGTGCCGCAGGGAGCTGATCTGCTGAAAGCCGTGGATGGTGTAGGCTGGAGCTGCTTC | SEQ ID No. 10 GATGAGTGGTCGAGGGCCAGTTGCAGAAGTGGTCGGCTCAATTCCGGGGATCCGTCGACC |
| araBAD (flanking homology) | E. coli | SEQ ID No. 11 ACTGTTTCTCCATACCCGTTTTTTTGGATGGAGTGAAACGGTGTAGGCTGGAGCTGCTTC | SEQ ID No. 12 CTGGTTTCGTTTGATTGGCTGTGGTTTTATACAGTCATTACATATGAATATCCTCCTTAG |

TABLE 2

List of strains.

| Strain | Description | Source |
|---|---|---|
| *Ambrosiozyma monospora* | | |
| NRRL Y-1484 | Type strain | ARS[1] |
| *Escherichia coli* K-12 | | |
| AB707 | F-, Wild type | CGSC[2] |
| BW25113 | lacI$^q$, rrnB$_{T14}$, ΔlacZ$_{W116}$, hsdR514, ΔaraBAD$_{AH33}$, ΔrhaBAD$_{LD78}$ | Datsenko and Wanner, 2000 |
| ZUC99 | ΔlyxK, lacI$^q$, rrnB$_{T14}$, ΔlacZ$_{W116}$, hsdR514, ΔaraBAD$_{AH33}$, Δrha-BAD$_{LD78}$ | This work |
| ZUC110 | ΔptsG, lacI$^q$, rrnB$_{T14}$, ΔlacIZ$_{W116}$, hsdR514, ΔaraBAD$_{AH33}$, Δrha-BAD$_{LD78}$ | This work |
| *Pantoea ananatis* | | |
| NRRL B-14773 | Type strain | ARS[1] |

[1] Agricultural Research Service Culture Collection, National Center for Agricultural Utilization Research, USDA-ARS.
[2] Coli Genetic Stock Center, Yale University.

TABLE 3

Conversion of L-arabinose to xylitol using the araA/rdte/alx1 operon.

| | L-Arabinose (g/L) | | Xylitol (g/L) | | % |
|---|---|---|---|---|---|
| Strain | 0 hr | 24 hrs | 0 hr | 24 hrs | Conversion[1] |
| BW25113/pATX208 | 10.5 | 6.6 ± 0.1 | 0.0 | 2.5 ± 0.5 | 24 |

[1] % conversion of L-arabinose to xylitol in 24 hours.

TABLE 4

Conversion of L-arabinose to xylitol using the P$_{BAD}$-araA/rdte/alx1 Operon.

| | L-Arabinose (g/L) | | Xylitol (g/L) | | % |
|---|---|---|---|---|---|
| Strain | 0 hr | 24 hrs | 0 hr | 24 hrs | Conversion[1] |
| BW25113/pATX210 | 10.8 | 5.7 ± 0.2 | 0.0 | 2.6 ± 0.2 | 25 ± 2 |

[1] % conversion of L-arabinose to xylitol in 24 hours.

TABLE 5

Conversion of xylitol to xylulose using *P. ananatis* L-xylulose reductase.

| | Xylitol (g/L) | | Xylulose (g/L) | | % |
|---|---|---|---|---|---|
| Strain | 0 hr | 24 hrs | 0 hr | 24 hrs | Conversion[1] |
| AB707/pATX200 | 9.9 | 6.6 ± 0.1 | 0.0 | 3.0 ± 0.1 | 31 ± 1 |
| AB707/pTTQ18 | 9.9 | 9.9 ± 0.1 | 0.0 | 0.0 ± 0.0 | 0 |

[1] % conversion of xylitol to xylulose in 24 hours.

TABLE 6

Accumulation of L-xylulose using the L-xylulokinase mutant.

| | | Xylitol | | | L-Xylulose | | |
|---|---|---|---|---|---|---|---|
| Strain | | 0 hr | 24 hrs | 72 hrs | 0 hr | 24 hrs | 72 hrs |
| ZUC99/pATX200 | g/L | 10.3 | 6.0 ± 0.3 | 2.7 ± 0.2 | 0.0 | 4.7 ± 0.5 | 6.1 ± 0.1 |
| | g/100 g sub[1] | 100 | 58 ± 3 | 26 ± 2 | 0 | 46 ± 5 | 59 ± 2 |
| AB707/pATX200 | g/L | 9.9 | 6.6 ± 0.1 | 0.0 ± 0.0 | 0.0 | 3.0 ± 0.1 | 0.0 ± 0.0 |
| | g/100g sub[1] | 100 | 67 ± 1 | 0 ± 0 | 0 | 31 ± 1 | 0 ± 0 |

[1] amount relative to the amount of xylitol added as a substrate, expressed in percent.

TABLE 7

Conversion of L-arabinose to xylitol using the araA/rdte/alx1 operon and the L-xylulokinase mutant.

| | L-Arabinose (g/L) | | Xylitol (g/L) | | % Con. | |
|---|---|---|---|---|---|---|
| Strain | 0 hr | 24 hrs | 0 hr | 24 hrs | % Con.[1] | of Cons.[2] |
| ZUC99/pATX210 | 10.3 | 5.6 ± 0.1 | 0.0 | 3.1 ± 0.1 | 30 ± 1 | 66 ± 2 |

[1] % conversion of total L-arabinose to xylitol in 24 hours.
[2] % conversion of consumed L-arabinose to xylitol in 24 hours.

TABLE 8

Conversion of L-arabinose to xylitol using the araA/rdte/plx1 operon and the L-xylulokinase mutant.

| | L-Arabinose (g/L) | | Xylitol (g/L) | | % |
|---|---|---|---|---|---|
| Strain | 0 hr | 24 hrs | 0 hr | 24 hrs | Conversion[1] |
| ZUC99/pATX216 | 10.3 | 6.6 ± 0.5 | 0.0 | 2.5 ± 0.2 | 23 ± 2 |

[1] % conversion of L-arabinose to xylitol in 24 hours.

TABLE 9

Conversion of L-arabinose to xylitol using glycerol as a co-substrate.

| | L-Arabinose (g/L) | | Glycerol (g/L) | | Xylitol (g/L) | | % | % Con. |
|---|---|---|---|---|---|---|---|---|
| Strain | 0 hr | 24 hrs | 0 hr | 24 hrs | 0 hr | 24 hrs | Con.[1] | of Cons.[2] |
| ZUC99/pATX210 | 9.8 | 0.3 ± 0.0 | 14.5 | 8.9 ± 0.3 | 0.0 | 10.6 ± 0.1 | 108 ± 1 | 112 ± 1 |

[1] % conversion of total L-arabinose to xylitol in 24 hours.
[2] % conversion of consumed L-arabinose to xylitol in 24 hours.

TABLE 10

Xylitol synthesis from L-arabinose and glucose mixture.

| Strain | L-Arabinose (g/L) 0 hr | L-Arabinose (g/L) 24 hrs | Glucose (g/L) 0 hr | Glucose (g/L) 24 hrs | Xylitol (g/L) 0 hr | Xylitol (g/L) 24 hrs | % Conversion[1] |
|---|---|---|---|---|---|---|---|
| ZUC110/pATX210 | 10.5 | 2.6 ± 0.3 | 10.6 | 4.6 ± 0.2 | 0.0 | 6.4 ± 0.3 | 60 ± 3 |
| ZUC99/pATX210 | 9.7 | 9.7 ± 0.1 | 10.5 | 7.1 ± 0.1 | 0.0 | 0.0 ± 0.0 | 0 ± 0 |

[1] % conversion of L-arabinose to xylitol in 24 hours.

We claim:

1. A recombinant L-arabinose-fermenting microorganism comprising heterologous polynucleotide sequences coding for L-xylulose reductase, D-tagatose 3-epimerase, and L-arabinose isomerase, wherein said microorganism expresses said heterologous polynucleotides at a sufficient functional level to be effective to produce xylitol from arabinose, and further wherein said microorganism is selected from the group consisting of a gram negative bacterium and a yeast.

2. The recombinant microorganism of claim 1 produced by transformation of a parent microorganism with said heterologous polynucleotide sequences coding for Lxylulose reductase, D-tagatose 3-epimerase, and L-arabinose isomerase, and further wherein said parent microorganism lacks one or more enzymes in the pathway for converting L-ribulose or L-xylulose or both to D-xylulose 5-phosphate and wherein said microorganism is *E. coli*.

3. The recombinant microorganism of claim 2 wherein said parent microorganism lacks ribulokinase (AraB) activity for the phosphorylation of L-ribulose to L-ribulose 5-phosphate.

4. The recombinant microorganism of claim 2 wherein said parent microorganism lacks L-xylulokinase (lyxK) activity for the phosphorylation of L-xylulose to L-xylulose 5-phosphate.

5. The recombinant microorganism of claim 2 wherein said parent microorganism lacks both ribulokinase (AraB) activity for the phosphorylation of L-ribulose to L-ribulose 5-phosphate, and L-xylulokinase (lyxK) activity for the phosphorylation of L-xylulose to L-xylulose 5-phosphate.

6. The recombinant microorganism of claim 2 wherein said parent microorganism lacks a ptsG gene or has an inactive ptsG gene.

7. The recombinant microorganism of claim 1 wherein said bacterium comprises a gram negative bacterium.

8. A nucleic acid construct comprising polynucleotide sequences coding for each of L-xylulose reductase, D-tagatose 3-epimerase, and L-arabinose isomerase, wherein said polynucleotide sequences are operably linked to one or more expression control sequences.

9. The nucleic acid construct of claim 8 comprising a plasmid.

10. A recombinant microorganism stably transformed with the nucleic acid construct of claim 8, and further wherein said microorganism is selected from the group consisting of a gram negative bacterium and a yeast.

11. The recombinant microorganism of claim 10 wherein said recombinant microorganism lacks one or more enzymes in the pathway for Converting L-ribulose or L-xylulose or both to D-xylulose 5-phosphate and wherein said microorganism is *E. coli*.

12. The recombinant microorganism of claim 11 wherein said recombinant microorganism lacks ribulokinase activity for the phosphorylation of L-ribulose to L-ribulose 5-phosphate.

13. The recombinant microorganism of claim 11 wherein said recombinant microorganism lacks L-xylulokinase (lyxK) activity for the phosphorylation of L-xylulose to L-xylulose 5-phosphate.

14. The recombinant microorganism of claim 11 wherein said recombinant microorganism lacks both ribulokinase (AraB) activity for the phosphorylation of L-ribulose to L-ribulose 5-phosphate, and L-xylulokinase (lyxK) activity for the phosphorylation of L-xylulose to L-xylulose 5-phosphate.

15. The recombinant microorganism of claim 11 wherein said recombinant microorganism lacks a ptsG gene or has an inactive ptsG gene.

16. The recombinant microorganism of claim 10 wherein Said bacterium comprises a gram negative bacterium.

17. The recombinant microorganism of claim 1 wherein said microorganism is *Escherichia coli*.

18. The recombinant microorganism of claim 1 wherein said microorganism is a yeast.

19. The recombinant microorganism of claim 10 wherein said microorganism is *Escherichia coli*.

20. The recombinant microorganism of claim 10 wherein said microorganism is a yeast.

21. A recombinant L-arabinose-fermenting *Escherichia coli* comprising heterologous polynucleotide sequences coding for L-xylulose reductase, D-tagatose 3-epimerase, and L-arabinose isomerase, wherein said *Escherichia coli* expresses said heterologous polynucleotides at a sufficient functional level to be effective to produce xylitol from arabinose, and further wherein said *Escherichia coli* lacks ribulokinase (AraB) activity for the phosphorylation of L-ribulose to L-ribulose 5-phosphate.

* * * * *